United States Patent [19]

Eicken et al.

[11] Patent Number: 5,416,103

[45] Date of Patent: May 16, 1995

[54] N-CYCLOHEX(EN)YL-PYRIDINE CARBOXAMIDES AND COMPOSITIONS CONTAINING THEM FOR CONTROLLING FUNGAL PESTS

[75] Inventors: Karl Eicken, Wachenheim; Eberhard Ammermann, Heppenheim; Gisela Lorenz, Neustadt, all of Germany

[73] Assignee: BASF Aktiengesellschaft, Ludwigshafen, Germany

[21] Appl. No.: 121,430

[22] Filed: Sep. 16, 1993

[30] Foreign Application Priority Data

Sep. 21, 1992 [DE] Germany ............... 42 31 519.0

[51] Int. Cl.[6] .................. C07D 213/82; A01N 43/40
[52] U.S. Cl. .................................. 514/355; 546/316
[58] Field of Search ..................... 546/316; 514/355

[56] References Cited

U.S. PATENT DOCUMENTS

| | | | |
|---|---|---|---|
| 3,402,241 | 9/1968 | von Schmeling et al. | 424/248 |
| 3,505,055 | 4/1970 | von Schmeling et al. | 504/266 |
| 3,862,966 | 1/1975 | Distler et al. | 260/347 |
| 3,969,510 | 7/1976 | Osieka et al. | 424/324 |
| 4,001,416 | 1/1977 | Pommer et al. | 424/266 |
| 4,134,987 | 1/1979 | Huppatz | 424/273 |
| 4,973,597 | 11/1990 | Robertson | 546/316 |

FOREIGN PATENT DOCUMENTS 1215066  12/1969  United Kingdom ............ 504/266

OTHER PUBLICATIONS

*Chem. Abst.*, vol. 110, No. 9, Feb. 27, 1989 (English abstract of PL-A 142442).
*ACTA Phytopathol.*, vol. 8, No. 3, 1973, pp. 269–282.
Pest Bio. and Phy. 34, 244–276 (1989) Substituted 2-Methylbanzanilides and Structurally Related Carboxamides . . . , White.

*Primary Examiner*—Bernard Dentz
*Assistant Examiner*—Zinna N. Davis
*Attorney, Agent, or Firm*—Keil & Weinkauf

[57] ABSTRACT

N-Cyclohex(en)ylcarboxamides of the formula I

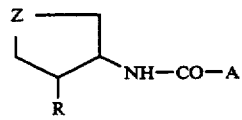

where:
R is substituted or unsubstituted alkyl, alkoxy, alkenyl, alkenyloxy, alkynyl, alkynyloxy, cycloalkyl, cycloalkenyl, cycloalkyloxy, cycloalkenyloxy, phenyl or benzyl;
Z is $CH_2CH_2$ or $CH=CH$;
A is one of the radicals A1 to A7:

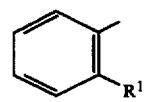

A1

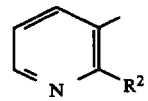

A2

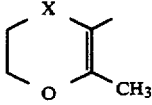

A3

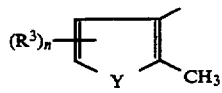

A4

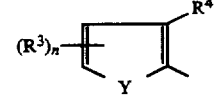

A5

(Abstract continued on next page.)

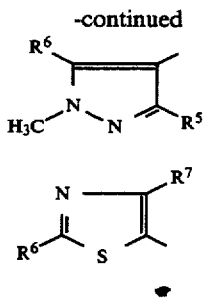
where
X is —$CH_2$—, —S—, —SO— or —$SO_2$—;
Y is —O— or —S—;
$R^1$, $R^2$, $R^4$, $R_5$ and $R^7$ are halogen, alkyl or haloalkyl;
$R^3$ and $R^6$ are hydrogen, halogen or alkyl;
n is 1 or 2;
methods of manufacturing them, agents containing them and the use thereof for controlling harmful fungi.
6 Claims, No Drawings

N-CYCLOHEX(EN)YL-PYRIDINE CARBOXAMIDES AND COMPOSITIONS CONTAINING THEM FOR CONTROLLING FUNGAL PESTS

The present invention relates to N-cyclohex(en)yl-carboxamides of the formula I

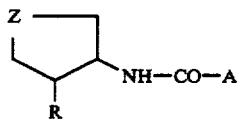

where
R is $C_2$-$C_{12}$-alkyl, $C_2$-$C_{12}$-alkoxy, $C_3$-$C_{12}$-alkenyl, $C_3$-$C_{12}$-alkenyloxy, $C_3$-$C_6$-alkynyl, $C_3$-$C_6$-alkynyloxy, it being possible for these groups to be partially or completely halogenated; $C_3$-$C_7$-cycloalkyl, $C_4$-$C_7$-cycloalkenyl, $C_3$-$C_7$-cycloalkyloxy or $C_4$-$C_7$-cycloalkenyloxy, it being possible for these rings to carry from one to three $C_1$-$C_4$-alkyl groups; phenyl or benzyl, it being possible for the phenyl rings in each case to carry from one to five halogen atoms and/or from one to three of the following radicals: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio or $C_1$-$C_4$-haloalkylthio;
Z is $CH_2CH_2$ or $CH=CH$;
A is a cyclic radical from the group of formulae A1 to A7

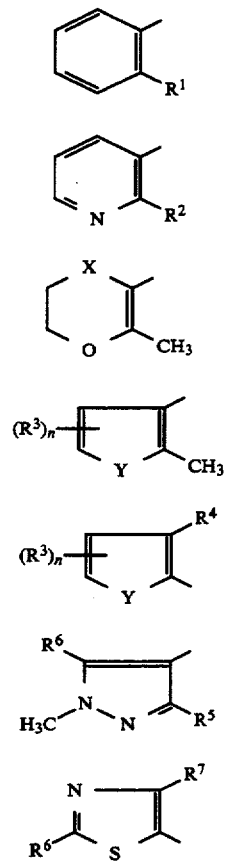

where
X is —$CH_2$—, —S—, —SO— or —$SO_2$—;
Y is —O— or —S—;
$R^1$, $R^2$, $R^4$, $R^5$ and $R^7$ are each halogen, $C_1$-$C_4$-alkyl or $C_1$-$C_4$-haloalkyl;
$R^3$ and $R^6$ are each hydrogen, halogen or $C_1$-$C_4$-alkyl;
n is 1 or 2, it being possible for the $R^3$ radicals to be different when n is 2.

The present invention also relates to processes for preparing these compounds, to compositions containing them and to methods of using them to control fungal pests.

The literature discloses N-cyclohexylcarboxamides with fungicidal properties (eg. N-(2-methylcyclohexyl)-2-chloronicotinamide in DE-A 24 17 216; N-cyclohexyl-2-methylbenzamide, N-cyclohexyl-3-methylthiophene-2-carboxamide, N-cyclohexyl-2,5-dimethylfuran-3-carboxamide, N-cyclohexyl-2-methyl-5,6-dihydro-1,4-oxathiine-3-carboxamide from Pestic. Biochem. Physiol. 34 (1989) 255).

It is an object of the present invention to provide novel compounds with fungicidal activity and an improved spectrum of action, especially against botrytis.

We have found that this object is achieved by the compounds I defined in the introduction. We have additionally found processes for preparing these compounds, compositions containing them and methods for using them for controlling fungal pests.

The compounds I are obtained in general by reacting a carbonyl halide of the formula II in a conventional way (eg. J. March, Advanced Organic Chemistry, 2nd Ed., 382 f, McGraw-Hill, 1977) in the presence of a base with cyclohexylamine of the formula III.

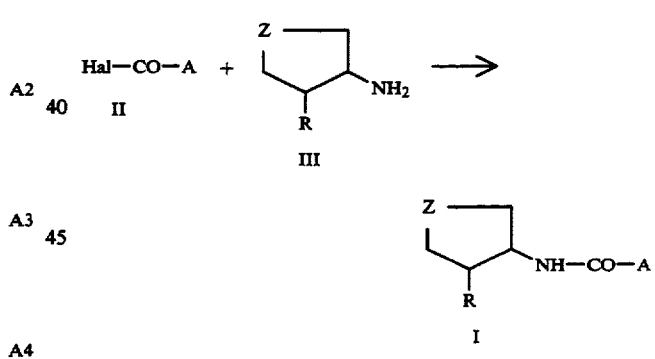

The Hal radical in the formula II is a halogen atom such as chlorine, bromine and iodine, especially chlorine or bromine.

This reaction is usually carried out at from −20° C. to 100° C., preferably 0° C. to 50° C.

Suitable solvents are: Aliphatic hydrocarbons such as pentane, hexane, cyclohexane and petroleum ether, aromatic hydrocarbons such as toluene, o-, m- and p-xylene, halohydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, alcohols such as methanol, ethanol, n-propanol, isopropanol, n-butanol and tert-butanol and dimethyl sulfoxide and dimethylformamide, particularly preferably toluene, xylene and methylene chloride.

It is also possible to use mixtures of the said solvents.

Suitable bases are, in general, inorganic compounds such as alkali metal and alkaline earth metal hydroxides such as lithium hydroxide, sodium hydroxide, potassium hydroxide and calcium hydroxide, alkali metal and alkaline earth metal oxides such as lithium oxide, sodium oxide, calcium oxide and magnesium oxide, alkali metal and alkaline earth metal hydrides such as lithium hydride, sodium hydride, potassium hydride and calcium hydride, alkali metal amides such as lithium amide, sodium amide and potassium amide, alkali metal and alkaline earth metal carbonates, such as lithium carbonate and calcium carbonate, and alkali metal bicarbonates such as sodium bicarbonate, and organometallic compounds, especially alkali metal alkyls such as methyllithium, butyllithium and phenyllithium, alkylmagnesium halides such as methylmagnesium chloride, and alkali metal and alkaline earth metal alcoholates such as sodium methanolate, sodium ethanolate, potassium ethanolate, potassium tert-butanolate and dimethoxymagnesium, in addition organic bases, eg. tertiary amines such as trimethylamine, triethylamine, triisopropylamine and N-methylpiperidine, pyridine, substituted pyridine such as collidine, lutidine and 4-dimethylaminopyridine, as well as bicyclic amines.

Triethylamine and pyridine are particularly preferred.

The amounts of the bases employed are generally equimolar with the compound II. The bases can, however, also be used in an excess of from 5 mol % to 30 mol %, preferably from 5 mol % to 10 mol % or, in the case of tertiary amines, where appropriate as solvent.

The precursors are generally reacted together in equimolar amounts. It may be advantageous for the yield to employ II in an excess of from 1 mol % to 20 mol %, preferably from 1 mol % to 10 mol %, relative to III.

The starting materials of the formula III required for preparing the compounds I disclosed in the literature (Tetrahedron Lett., Vol. 32 (1991) 1695; Houben-Weyl, Methoden der org. Chemie, Vol. 11/1, 382 f. and 611 f.; J. Chem. Soc. C. 10 (1971) 1805; J. Org. Chem. 53 (1988) 4852; Tetrahedron 23 (1967) 2421; Tetrahedron 47 (1991) 3075) or they can be prepared as described in the cited literature. The cis/trans mixtures of the compounds III which in some cases result from the reaction can in general be separated by distillation.

Suitable compounds of the formula I for use in fungicidal compositions are those in which the substituents have the following meanings:

R $C_2$–$C_{12}$-alkyl such as ethyl and straight-chain or branched propyl, butyl, pentyl, hexyl, heptyl, octyl, nonyl, decyl, undecyl and dodecyl, particularly straight-chain or branched $C_3$—$C_{10}$-alkyl such as propyl, 1-methylethyl, butyl, 1-methylpropyl, 2-methylpropyl, 1,1-dimethylethyl, n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-3-methylpropyl, n-heptyl, 1-methylhexyl, 1-ethylpentyl, 2-ethylpentyl, 1-propylbutyl, octyl, 1-methylheptyl, 2-methylheptyl, 1-ethylhexyl, 2-ethylhexyl, 1-propylpentyl, 2-propylpentyl, nonyl, 1-methyloctyl, 2-methyloctyl, 1-ethylheptyl, 2-ethylheptyl, 1-propylhexyl, 2-propylhexyl, decyl, 1-methylnonyl, 2-methylnonyl, 1-ethyloctyl, 2-ethyloctyl, 1-propylheptyl and 2-propylheptyl, especially propyl, 1-methylethyl, butyl, 1-methylbutyl, 2-methylbutyl, 1,1-dimethylethyl, pentyl, 1-methylbutyl, hexyl, heptyl and 1-methylheptyl, it being possible for these groups to be partially or completely halogenated, ie. the hydrogen atoms in these groups can be partially or completely replaced by halogen atoms such as fluorine, chlorine and bromine, especially fluorine and chlorine, for example haloalkyl such chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl; $C_2$–$C_{12}$-alkoxy such as ethoxy and straight-chain or branched propyloxy, butyloxy, pentyloxy, hexyloxy, heptyloxy, octyloxy, nonyloxy, decyloxy, undecyloxy and dodecyloxy, particularly straight-chain or branched $C_2$–$C_{10}$-alkoxy such as ethoxy, propoxy, 1-methylethoxy, butoxy, 1-methylpropoxy, 2-methylpropoxy, 1,1-dimethylethoxy, n-pentyloxy, 1-methylbutoxy, 2-methylbutoxy, 3-methylbutoxy, 1,2-dimethylpropoxy, 1-ethylpropoxy, n-hexyloxy, 1-methylpentyloxy, 2-methylpentyloxy, 3-methylpentyloxy, 4-methylpentyloxy, 1,2-dimethylbutoxy, 1,3-dimethylbutoxy, 2,3-dimethylbutoxy, 1,2-dimethylbutoxy, 2,2-dimethylbutoxy, 3,3-dimethylbutoxy, 1,1,2-trimethylpropoxy, 1,2,2-trimethylpropoxy, 1-ethylbutoxy, 2-ethyibutoxy, 1-ethyl-2-methylpropoxy, n-heptyloxy, 1-methylhexyloxy, 2-methylhexyloxy, 3-methylhexyloxy, 4-methylhexyloxy, 5-methylhexyloxy, 1-ethylpentyloxy, 2-ethylpentyloxy, 1-propylbutoxy, octyloxy, 1-methylheptyloxy, 2-methylheptyloxy, 1-ethylhexyloxy, 2-ethylhexyloxy, 1-propylpentyloxy, 2-propylpentyloxy, nonyloxy, 1-methyloctyloxy, 2-methyloctyloxy, 1-ethylheptyloxy, 2-ethylheptyloxy, 1-propylhexyloxy, 2-propylhexyloxy, decyloxy, 1-methylnonyloxy, 2-methylnonyloxy, 1-ethyloctyloxy, 2-ethyloctyloxy, 1-propylheptyloxy and 2-propylheptyloxy, especially ethoxy, propyloxy, 1-methylethoxy, butyloxy, 1-methylpropyloxy, 2-methylpropyloxy, 1,1-dimethylethoxy, pentyloxy, hexyloxy and 2-ethylhexyloxy, it being possible for these groups to be partially or completely halogenated, ie. the hydrogen atoms in these groups can be partially or completely replaced by halogen atoms such as fluorine, chlorine and bromine, especially fluorine and chlorine, for example haloalkoxy such as chloromethyloxy, dichloromethyloxy, trichloromethyloxy, fluoromethyloxy, difluoromethyloxy, trifluoromethyloxy, chlorofluoromethyloxy, dichlorofluoromethyloxy, chlorodifluoromethyloxy, 1-fluoroethyloxy, 2-fluoroethyloxy, 2,2-difluoroethyloxy, 2,2,2-trifluoroethyloxy, 2-chloro-2-fluoroethyloxy, 2-chloro-2,2-difluoroethyloxy, 2,2-dichloro-2-fluoroethyloxy, 2,2,2-trichloroethyloxy and pentafluoroethyloxy; $C_3$–$C_{12}$-alkenyl such as straight-chain or branched propenyl, butenyl, pentenyl, hexenyl, heptenyl, octenyl, nonenyl, decenyl, undecenyl and dodecenyl, particularly straight-chain or branched $C_3$–$C_{10}$-alkenyl such as 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 1-methyl-3-pentenyl, 2-methyl-3-pentenyl, 1-methyl-2-hexenyl, 2-methyl-2-hexenyl, 1-methyl-3-hexenyl, 2-methyl-3-hexenyl, 1-ethyl-2-pentenyl, 2-ethyl-2-pentenyl, 1-ethyl-3-pentenyl, 2-ethyl-3-pentenyl, 1-methyl-2-heptenyl, 2-methyl-2-heptenyl, 1-methyl-3-heptenyl, 2-methyl-3-heptenyl, 1-ethyl-2-hexenyl, 2-ethyl-2-hexenyl, 1-ethyl-3-hexenyl, 2-ethyl-3-hexenyl, 1-methyl-2-octenyl, 2-methyl-2-octenyl, 1-methyl-3-octenyl, 2-methyl-3-octenyl, 1-ethyl-2-heptenyl, 2-ethyl-2-heptenyl, 1-ethyl-3-heptenyl, 2-ethyl-3-heptenyl, 1-ethyl-2-octenyl, 2-ethyl-2-octenyl, 1-ethyl-3-octenyl and 2-ethyl-3-octenyl, especially 1-propenyl, 2-propenyl, 1-methylethenyl, 1-methyl-2-propenyl, 2-methyl-2-propenyl, 1-ethyl-2-propenyl, 1-methyl-2-butenyl, 1-ethyl-2-butenyl, 1-(1-methylethyl)-2-butenyl, 1-butyl-2-butenyl, 1-methyl-2-pentenyl and 1,4-dimethyl-2-pentenyl, it being possible for these groups to be partially or completely halogenated, i.e. the hydrogen atoms in these groups can be partially or completely replaced by halogen atoms such as fluorine, chlorine and bromine, especially fluorine and chlorine, in particular 3-chloro-2-propenyl, 2,3-dichloro-2-propenyl and 2,3,3-trichloro-2-propenyl; $C_3$–$C_{12}$-alkenyloxy such as straight-chain or branched propenyloxy, butenyloxy, pentenyloxy, hexenyloxy, heptenyloxy, octenyloxy, nonenyloxy, decenyloxy, undecenyloxy and dodecenyloxy, particularly straight-chain or branched $C_3$–$C_{10}$-alkenYloxY such as 2-propenyloxy, 2-butenyloxy, 3-butenyloxy, 1-methyl-2-propenyloxy, 2-methyl-2-propenyloxy, 2-pentenyloxy, 3-pentenyloxy, 4-pentenyloxy, 1-methyl-2-butenyloxy, 2-methyl-2-butenyloxy, 3-methyl-2-butenyloxy, 1-methyl-3-butenyloxy, 2-methyl-3-butenyloxy, 3-methyl-3-butenyloxy, 1,1-dimethyl-2-propenyloxy, 1,2-dimethyl-2-propenyloxy, 1-ethyl-2-propenyloxy, 2-hexenyloxy, 3-hexenyloxy, 4-hexenyloxy, 5-hexenyloxy, 1-methyl-2-pentenyloxy, 2-methyl-2-pentenyloxy, 3-methyl-2-pentenyloxy, 4-methyl-2-pentenyloxy, 2-methyl-3-pentenyloxy, 3-methyl-3-pentenyloxy, 4-methyl-3-pentenyloxy, 1-methyl-4-pentenyloxy, 2-methyl-4-pentenyloxy, 3-methyl-4-pentenyloxy, 4-methyl-4-pentenyloxy, 1,1-dimethyl-2-butenyloxy, 1,1-dimethyl-3-butenyloxy, 1,2-dimethyl-2-butenyloxy, 1,2-dimethyl-3-butenyloxy, 1,3-dimethyl-2-butenyloxy, 1,3-dimethyl-3-butenyloxy, 2,2-dimethyl-3-butenyloxy, 2,3-dimethyl-2-butenyloxy, 2,3-dimethyl-3-butenyloxy, 1-ethyl-2-butenyloxy, 1-ethyl-3-butenyloxy, 2-ethyl-2-butenyloxy, 2-ethyl-3-butenyloxy, 1,1,2-trimethyl-2-propenyloxy, 1-ethyl-1-methyl-2-propenyloxy, 1-ethyl-2-methyl-2-propenyloxy, 1-methyl-2-pentenyloxy, 2-methyl-2-pentenyloxy, 1-methyl-3-pentenyloxy, 2-methyl-3-pentenyloxy, 1-methyl-2-hexenyloxy, 2-methyl-2-hexenyloxy, 1-methyl-3-hexenyloxy, 2-methyl-3-hexenyloxy, 1-ethyl-2-hexenyloxy, 2-ethyl-2-pentenyloxy, 1-ethyl-3-pentenyloxy, 2-ethyl-3-pentenyloxy, 1-methyl-2-hexenyloxy, 2-methyl-2-heptenyloxy, 1-methyl-3-heptenyloxy, 2-methyl-3-heptenyloxy, 1-ethyl-2-hexenyloxy, 2-ethyl-2-hexenyloxy, 1-ethyl-3-hexenyloxy, 2-ethyl-3-hexenyloxy, 1-methyl-2-oxtenyloxy 2-ethyl-2-oxtenyloxy, 1-ethyl-3-oxtenyloxy 2-ethyl-3-octenyloxy, especially 2-propenyloxy, 1-methyl-2-propenyloxy, 2-methyl-2-propenyloxy, 2-pentenyloxy, 3-pentenyloxy, 1-methyl-2-butenyloxy and 1-methyl-2-pentenyloxy, it being possible for these groups to be partially or completely halogenated, i.e. the hydrogen atoms in these groups can be partially or completely replaced by halogen atoms such as fluorine, chlorine and bromine, especially fluorine and chlorine, in particular 3-chloro-2-propenyloxy, 2,3-dichloro-2-propenyloxy and 2,3,3-trichloro-2-propenyloxy; $C_3$–$C_6$-alkynyl such as 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-alkynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,2-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl- 1-methyl-2-propynyl, in particular 2-propynyl, 2-butynyl and 3-butynyl, it being possible for these groups to be partially or completely halogenated, i.e. the hydrogen atoms in these groups can be partially or completely replaced by halogen atoms such as fluorine, chlorine and bromine, especially fluorine and chlorine, for example 3-chloro-2-propynyl, 3-chloro-2-butynyl and 4-chloro-3-butynyl; $C_3$–$C_6$-alkynyloxy such as 2-propynyloxy, 2-butynyloxy, 3-butynyloxy, 1-methyl-2-propynyloxy, 2-pentynyloxy, 3-pentynyloxy, 4-pentynyloxy, 1-methyl-3-butynyloxy, 2-methyl-3-butynyloxy, 1-methyl-2-butynyloxy, 1,1-dimethyl-2-propynyloxy, 1-ethyl-2-propynyloxy, 2-hexynyloxy, 3-hexynyloxy, 4-alkynyloxy, 5-hexynyloxy, 1-methyl-2-pentynyloxy, 1-methyl-3-pentynyloxy, 1-methyl-4-pentynyloxy, 2-methyl-3-pentynyloxy, 2-methyl-4-pentynyloxy, 3-methyl-4-pentynyloxy, 4-methyl-3-pentynyloxy, 1,1-dimethyl-2-butynyloxy, 1,1-dimethyl-3-butynyloxy, 1,2-dimethyl-3-butynyloxy, 2,2-dimethyl-3-butynyloxy, 1-ethyl-2-butynyloxy, 1-ethyl-3-butynyloxy, 2-ethyl-3-butynyloxy and 1-ethyl-l-methyl-2-propynyloxy, preferably 2-propynyloxy, 2-butynyloxy, 1-methyl-2-propynyloxy and 1-methyl-2-butynyloxy, it being possible for these groups to be partially or completely halogenated, i.e. the hydrogen atoms in these groups can be partially or completely replaced by halogen atoms such as fluorine, chlorine and bromine, especially fluorine and chlorine, for example 3-chloro-2-propynyloxy, 3-chloro-2-butynyloxy and 4-chloro-3-butynyloxy; $C_3$–$C_7$-cycloalkyl such as cyclopropyl, cyclobutyl, cyclopentyl, cyclohexyl and cycloheptyl, it being possible for these rings to carry from one to three $C_1$–$C_7$-alkyl groups such as methyl, ethyl, propyl, 1-methylethyl, butyl, 1-methylpropyl, 2-methylpropyl and 1,1-dimethylethyl; $C_4$–$C_7$-cycloalkenyl such as cyclobutenyl, cyclopentenyl, cyclohexenyl and cycloheptenyl, it being possible for these rings to carry from one to three $C_1$–$C_4$-alkyl groups such as methyl, ethyl, propyl, 1-methylethyl, butyl, 1-methylpropyl, 2-methylpropyl and 1,1-dimethylethyl; $C_3$–$C_7$-cycloalkyloxy such as cyclopropyloxy, cyclobutyloxy, cyclopentyloxy, cyclohexyloxy and cycloheptyloxy, it being possible for these rings to carry from one to three $C_1$–$C_4$-alkyl groups such as methyl, ethyl, propyl, 1-methylethyl, butyl, 1-methylpropyl, 2-methylpropyl and 1,1-dimethylethyl; or $C_4$–$C_7$-cycloalkenyloxy such as 1-cyclobutenyloxy, 2-cyclobutenyloxy, 1-cyclopententyloxy, 2-cyclopentenyloxy, 3-cyclopentenyloxy, 1-cyclohexenyloxy, 2-cyclohexenyloxy, 3-cyclohexenyloxy, 1-cycloheptenyloxy, 2-cycloheptenyloxy, 3-cycloheptenyloxy and 4-cycloheptenyloxy, it being possible for these rings to carry from one to three $C_1$–$C_4$-alkyl groups such as methyl, ethyl, propyl, 1-methylethyl, butyl, 1-methylpropyl, 2-methylpropyl and 1,1-dimethylethyl; phenyl, which can carry from one to five halogen atoms such as fluorine, chlorine, bromine and iodine, especially fluorine, chlorine and bromine, and/or from one to three of the following radicals: $C_1$–$C_4$-alkyl as mentioned above; $C_1$–$C_4$-haloalkyl as mentioned above; $C_1$–$C_4$-alkoxy as mentioned above; $C_1$–$C_4$-haloalkoxy as mentioned above; $C_1$–$C_4$-alkylthio such as methylthio, ethylthio, propylthio, 1-methylethylthio, butylthio, 1-methylpropylthio, and 1,1-dimethylpropylthio, ethylthio; or $C_1$–$C_4$-haloalkylthio, particularly $C_1$–$C_2$-haloalkylthio such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluorotethylthio, 2,2,2-trichloroethylthio and pentafluoroethylthio;

A is a cyclic radical from the group of formulae A1 to A7

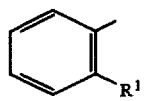

A1

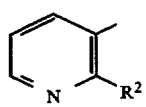

A2

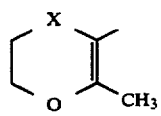

A3

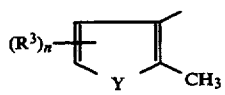

A4

-continued

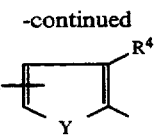

A5

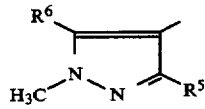

A6

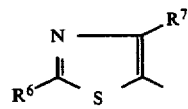

A7 where

X is —$CH_2$—, —S—, —SO— or —$SO_2$—;

Y is —O— or —S—;

$R^1$, $R^2$, $R^4$, $R^5$ and $R^7$ are each, independently of one another, halogen such as fluorine, chlorine and bromine, $C_1$–$C_4$-alkyl as mentioned above, or $C_1$–$C_4$-haloalkyl as mentioned above, $R^3$ and $R^6$ are each, independently of one another, hydrogen, halogen such fluorine, chlorine and bromine or $C_1$–$C_4$-alkyl as mentioned above;

n is 1 or 2, it being possible for the $R^3$ radicals to be different when n is 2.

Compounds of the formula I which are particularly preferred in respect of the biological effect are those where R has the abovementioned meanings and A is a cyclic radical from the group of formulae A1 to A7, where X and Y have the abovementioned meanings, and the substituents are the following radicals:

$R^1$ halogen such as fluorine, chlorine and bromine, methyl or $C_1$-haloalkyl such as chloromethyl, dichloromethyl, trichloromethyl, fluoromethyl, difluoromethyl, trifluoromethyl, chlorofluoromethyl, dichlorofluoromethyl and chlorodifluoromethyl;

$R^2$ halogen such as fluorine, chlorine and bromine or $C_1$-haloalkyl such as chloromethyl, dichloromethyl, trichloromethyl, fluoromethyl, difluoromethyl, trifluoromethyl, chlorofluoromethyl, dichlorofluoromethyl and chlorodifluoromethyl;

$R^3$ hydrogen or methyl;

n 1 or 2, it being possible for the $R^3$ radicals to be different when n is 2;

$R^4$ halogen such as fluorine, chlorine and bromine or methyl;

$R^5$ methyl or $C_1$-haloalkyl such as chloromethyl, dichloromethyl, trichloromethyl, fluoromethyl, difluoromethyl, trifluoromethyl, chlorofluoromethyl, dichlorofluoromethyl and chlorodifluoromethyl;

$R^6$ hydrogen, halogen such as fluorine, chlorine and bromine or methyl;

$R^7$ halogen such as fluorine, chlorine and bromine, methyl or $C_1$-haloalkyl such as chloromethyl, dichloromethyl, trichloromethyl, fluoromethyl, difluoromethyl, trifluoromethyl, chlorofluoromethyl, dichlorofluoromethyl and chlorodifluoromethyl.

Particularly preferred compounds of the formula I are those in which R has the abovementioned meanings, and A is a cyclic radical from the group of formulae A1 to A7, where X and Y have the abovementioned meanings, and the substituents are the following groups:

$R^1$ chlorine, bromine, iodine, methyl or trifluoromethyl;
$R^2$ chlorine or trifluoromethyl;
$R^3$ hydrogen or methyl;
n 1 or 2, it being possible for the $R^3$ radicals to be different when n is 2;
$R^4$ chlorine or methyl;
$R^5$ methyl, difluoromethyl or trifluoromethyl;
$R^6$ hydrogen, chlorine or methyl;
$R^7$ chlorine, methyl or trifluoromethyl.

In respect of the biological effect, particularly preferred compounds I are also those where the groups R and NHCOA are arranged trans with respect to one another.

Particularly preferred compounds of the formula I are:
compounds I where
R is ethyl, propyl, isopropyl, butyl, isobutyl, sec-butyl, 2-ethylbutyl, cyclopentyl, cyclohexyl, 2-cyclopentenyl, 1-cyclohexenyl, phenyl or benzyl, it being possible for phenyl radicals in each case also to carry from one to three of the following groups: halogen, $C_1-C_4$-alkyl, $C_1-C_4$-haloalkyl, $C_1-C_4$-alkoxy, $C_1-C_4$-haloalkoxy and $C_1-C_4$-alylthio, preferably compounds I where
R is ethyl, propyl, isopropyl, butyl, isobutyl, sec-butyl, cyclohexyl, 1-cyclohexenyl, phenyl or benzyl, it being possible for the phenyl radicals in each case also to carry from one to three of the following groups: halogen, $C_1-C_2$-alkyl, $C_1-C_2$-haloalkyl, $C_1-C_2$-alkoxy, $C_1-C_2$-haloalkoxy and $C_1-C_2$-alkylthio, in particular compounds I where
R is ethyl, propyl, isopropyl, butyl, isobutyl, sec-butyl, cyclohexyl, 1-cyclohexenyl, phenyl or benzyl, it being possible for the phenyl radicals in each case also to carry from one to three of the following groups: halogen, $C_1-C_2$-alkyl, $C_1-C_2$-haloalkyl, $C_1-C_2$-alkoxy and $C_1-C_2$-haloalkoxy.

Compounds I where
A is A1, A2, A3, A4, A6 or A7,
preferably compounds I where
A is A1, A2, A3, A4 (Y=o), A6 or A7.
Compounds I where
A is A1,
preferably compounds I where
A is A1 and
$R^1$ is chlorine, bromine, methyl and trifluoromethyl, and
especially compounds I where
A is A1 and
$R^1$ is bromine, methyl and trifluoromethyl and
R is sec-butyl, 2-cyclopentenyl and phenyl.
Compounds I where
A is A2,
preferably compounds I where
A is A2 and
$R^2$ is chlorine and
especially compounds I where
A is A2,
$R^2$ is chlorine,
Z is $CH_2CH_2$ and
R is ethyl, propyl, isopropyl, butyl, isobutyl, sec-butyl, cyclohexyl, 1-cyclohexenyl, phenyl or benzyl, it being possible for the phenyl radicals in each case also to carry from one to three of the following groups: halogen, $C_1-C_4$-alkyl, $C_1-C_4$-haloalkyl and $C_1-C_4$-alkoxy.

Compounds I where
A is A3,
preferably compounds I where
A is A3,
X is oxygen and sulfur and
Z is $CH_2CH_2$,
expecially compounds I where
A is A3,
X is oxygen and sulfur,
Z is $CH_2CH_2$ and
R is sec-butyl.
Compounds I where
A is A4 and
Y is oxygen,
preferably compounds I where
A is A4 and
Y is oxygen and
$A^3$ is methyl,
especially compounds I where
A is A4,
Y is oxygen,
$R^3$ is methyl,
Z is $CH_2CH_2$ and
R is sec-butyl and 1-cyclohexenyl.
Compounds I where
A is A6,
preferably compounds I where
A is A6 and
$R^5$ and $R^6$ are each methyl,
especially compounds I where
A is A6,
$R^5$ and $R^6$ are each methyl,
Z is $CH_2CH_2$ and
R is 1-cyclohexenyl.
Compounds I where
A is A7,
preferably compounds I where
A is A7 and
$R^6$ and $R^7$ are each, independently of one another, methyl and trifluoromethyl,
especially compounds I where
A is A7 and
$R^6$ and $R^7$ are each, independently of one another, methyl and trifluoromethyl,
Z is $CH_2CH_2$ and
R is propyl, butyl, sec-butyl, cyclohexyl, 1-cyclohexenyl, phenyl or benzyl, it being possible for the phenyl radicals in each case also to carry from one to three of the following groups: halogen, $C_1-C_4$-alkyl, $C_1-C_4$-haloalkyl and $C_1-C_4$-alkoxy.

Particularly preferred compounds of the formula I are compiled in the following Tables A to G.

TABLE A

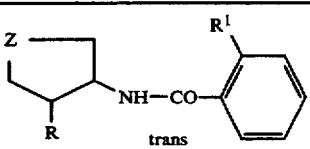

I.1

| $R^1$ | R | Z |
|---|---|---|
| $CF_3$ | $C_2H_5$ | $CH_2CH_2$ |
| $CF_3$ | i-$C_3H_7$ | $CH_2CH_2$ |
| $CF_3$ | n-$C_3H_7$ | $CH_2CH_2$ |
| $CF_3$ | n-$C_4H_9$ | $CH_2CH_2$ |
| $CF_3$ | sec.-$C_4H_9$ | $CH_2CH_2$ |

TABLE A-continued

I.1

| R¹ | R | Z |
|---|---|---|
| CF₃ | i-C₄H₉ | CH₂CH₂ |
| CF₃ | tert.-C₄H₉ | CH₂CH₂ |
| CF₃ | n-C₅H₁₁ | CH₂CH₂ |
| CF₃ | sec.-C₅H₁₁ | CH₂CH₂ |
| CF₃ | n-C₆H₁₃ | CH₂CH₂ |
| CF₃ | n-C₇H₁₅ | CH₂CH₂ |
| CF₃ | sec.-C₇H₁₅ | CH₂CH₂ |
| CF₃ | 1-Methylvinyl | CH₂CH₂ |
| CF₃ | 2-Methylvinyl | CH₂CH₂ |
| CF₃ | Allyl | CH₂CH₂ |
| CF₃ | 2-Methylallyl | CH₂CH₂ |
| CF₃ | 2-Ethylallyl | CH₂CH₂ |
| CF₃ | 1-Methylallyl | CH₂CH₂ |
| CF₃ | l-Ethylallyl | CH₂CH₂ |
| CF₃ | 1-Methyl-2-butenyl | CH₂CH₂ |
| CF₃ | i-Ethyl-2-butenyl | CH₂CH₂ |
| CF₃ | Cyclopropyl | CH₂CH₂ |
| CF₃ | Cyclobutyl | CH₂CH₂ |
| CF₃ | Cyclopentyl | CH₂CH₂ |
| CF₃ | Cyclohexyl | CH₂CH₂ |
| CF₃ | 2-Cyclopentenyl | CH₂CH₂ |
| CF₃ | 1-Cyclopentenyl | CH₂CH₂ |
| CF₃ | 2-Cyclohexenyl | CH₂CH₂ |
| CF₃ | 1-Cyclohexenyl | CH₂CH₂ |
| CF₃ | Phenyl | CH₂CH₂ |
| CH₃ | C₂H₅ | CH₂CH₂ |
| CH₃ | i-C₃H₇ | CH₂CH₂ |
| CH₃ | n-C₃H₇ | CH₂CH₂ |
| CH₃ | n-C₄H₉ | CH₂CH₂ |
| CH₃ | sec.-C₄H₉ | CH₂CH₂ |
| CH₃ | i-C₄H₉ | CH₂CH₂ |
| CH₃ | tert.-C₄H₉ | CH₂CH₂ |
| CH₃ | n-C₅H₁₁ | CH₂CH₂ |
| CH₃ | sec.-C₅H₁₁ | CH₂CH₂ |
| CH₃ | n-C₆H₁₃ | CH₂CH₂ |
| CH₃ | n-C₇H₁₅ | CH₂CH₂ |
| CH₃ | sec.-C₇H₁₅ | CH₂CH₂ |
| CH₃ | 1-Methylvinyl | CH₂CH₂ |
| CH₃ | 2-Methylvinyl | CH₂CH₂ |
| CH₃ | Allyl | CH₂CH₂ |
| CH₃ | 2-Methylallyl | CH₂CH₂ |
| CH₃ | 2-Ethylallyl | CH₂CH₂ |
| CH₃ | 1-Methylallyl | CH₂CH₂ |
| CH₃ | l-Ethylallyl | CH₂CH₂ |
| CH₃ | 1-Methyl-2-butenyl | CH₂CH₂ |
| CH₃ | 1-Ethyl-2-butenyl | CH₂CH₂ |
| CH₃ | Cyclopropyl | CH₂CH₂ |
| CH₃ | Cyclobutyl | CH₂CH₂ |
| CH₃ | Cyclopentyl | CH₂CH₂ |
| CH₃ | Cyclohexyl | CH₂CH₂ |
| CH₃ | 2-Cyclopentenyl | CH₂CH₂ |
| CH₃ | 1-Cyclopentenyl | CH₂CH₂ |
| CH₃ | 2-Cyclohexenyl | CH₂CH₂ |
| CH₃ | 1-Cyclohexenyl | CH₂CH₂ |
| CH₃ | Phenyl | CH₂CH₂ |
| Br | C₂H₅ | CH₂CH₂ |
| Br | i-C₃H₇ | CH₂CH₂ |
| Br | n-C₃H₇ | CH₂CH₂ |
| Br | n-C₄H₉ | CH₂CH₂ |
| Br | sec.-C₄H₉ | CH₂CH₂ |
| Br | i-C₄H₉ | CH₂CH₂ |
| Br | tert.-C₄H₉ | CH₂CH₂ |
| Br | n-C₅H₁₁ | CH₂CH₂ |
| Br | sec.-C₅H₁₁ | CH₂CH₂ |
| Br | n-C₆H₁₃ | CH₂CH₂ |
| Br | n-C₇H₁₅ | CH₂CH₂ |
| Br | sec.-C₇H₁₅ | CH₂CH₂ |
| Br | 1-Methylvinyl | CH₂CH₂ |
| Br | 2-Methylvinyl | CH₂CH₂ |
| Br | Allyl | CH₂CH₂ |
| Br | 2-Methylallyl | CH₂CH₂ |
| Br | 2-Ethylallyl | CH₂CH₂ |
| Br | 1-Methylallyl | CH₂CH₂ |
| Br | l-Ethylallyl | CH₂CH₂ |
| Br | 1-Methyl-2-butenyl | CH₂CH₂ |
| Br | l-Ethyl-2-butenyl | CH₂CH₂ |
| Br | Cyclopropyl | CH₂CH₂ |
| Br | Cyclobutyl | CH₂CH₂ |
| Br | Cyclopentyl | CH₂CH₂ |
| Br | Cyclohexyl | CH₂CH₂ |
| Br | 2-Cyclopentenyl | CH₂CH₂ |
| Br | 1-Cyclopentenyl | CH₂CH₂ |
| Br | 2-Cyclohexenyl | CH₂CH₂ |
| Br | 1-Cyclohexenyl | CH₂CH₂ |
| Br | Phenyl | CH₂CH₂ |
| CF₃ | C₂H₅ | CH=CH |
| CF₃ | i-C₃H₇ | CH=CH |
| CF₃ | n-C₃H₇ | CH=CH |
| CF₃ | n-C₄H₉ | CH=CH |
| CF₃ | sec.-C₄H₉ | CH=CH |
| CF₃ | i-C₄H₉ | CH=CH |
| CF₃ | tert.-C₄H₉ | CH=CH |
| CF₃ | n-C₅H₁₁ | CH=CH |
| CF₃ | sec.-C₅H₁₁ | CH=CH |
| CF₃ | n-C₆H₁₃ | CH=CH |
| CF₃ | n-C₇H₁₅ | CH=CH |
| CF₃ | sec.-C₇H₁₅ | CH=CH |
| CF₃ | 1-Methylvinyl | CH=CH |
| CF₃ | 2-Methylvinyl | CH=CH |
| CF₃ | Allyl | CH=CH |
| CF₃ | 2-Methylallyl | CH=CH |
| CF₃ | 2-Ethylallyl | CH=CH |
| CF₃ | 1-Methylallyl | CH=CH |
| CF₃ | l-Ethylallyl | CH=CH |
| CF₃ | 1-Methyl-2-butenyl | CH=CH |
| CF₃ | l-Ethyl-2-butenyl | CH=CH |
| CF₃ | Cyclopropyl | CH=CH |
| CF₃ | Cyclobutyl | CH=CH |
| CF₃ | Cyclopentyl | CH=CH |
| CF₃ | Cyclohexyl | CH=CH |
| CF₃ | 2-Cyclopentenyl | CH=CH |
| CF₃ | 1-Cyclopentenyl | CH=CH |
| CF₃ | 2-Cyclohexenyl | CH=CH |
| CF₃ | 1-Cyclohexenyl | CH=CH |
| CF₃ | Phenyl | CH=CH |
| CH₃ | C₂H₅ | CH=CH |
| CH₃ | i-C₃H₇ | CH=CH |
| CH₃ | n-C₃H₇ | CH=CH |
| CH₃ | n-C₄H₉ | CH=CH |
| CH₃ | sec.-C₄H₉ | CH=CH |
| CH₃ | i-C₄H₉ | CH=CH |
| CH₃ | tert.-C₄H₉ | CH=CH |
| CH₃ | n-C₅H₁₁ | CH=CH |
| CH₃ | sec.-C₅H₁₁ | CH=CH |
| CH₃ | n-C₆H₁₃ | CH=CH |
| CH₃ | n-C₇H₁₅ | CH=CH |
| CH₃ | sec.-C₇H₁₅ | CH=CH |
| CH₃ | 1-Methylvinyl | CH=CH |
| CH₃ | 2-Methylvinyl | CH=CH |
| CH₃ | Allyl | CH=CH |
| CH₃ | 2-Methylallyl | CH=CH |
| CH₃ | 2-Ethylallyl | CH=CH |
| CH₃ | 1-Methylallyl | CH=CH |
| CH₃ | l-Ethylallyl | CH=CH |
| CH₃ | 1-Methyl-2-butenyl | CH=CH |
| CH₃ | l-Ethyl-2-butenyl | CH=CH |
| CH₃ | Cyclopropyl | CH=CH |
| CH₃ | Cyclobutyl | CH=CH |
| CH₃ | Cyclopentyl | CH=CH |
| CH₃ | Cyclohexyl | CH=CH |
| CH₃ | 2-Cyclopentenyl | CH=CH |
| CH₃ | 1-Cyclopentenyl | CH=CH |
| CH₃ | 2-Cyclohexenyl | CH=CH |
| CH₃ | 1-Cyclohexenyl | CH=CH |
| CH₃ | Phenyl | CH=CH |
| Br | C₂H₅ | CH=CH |

TABLE A-continued

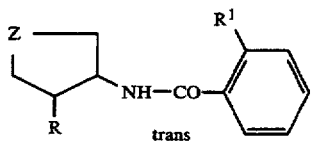

I.1

| R¹ | R | Z |
|---|---|---|
| Br | i-C$_3$H$_7$ | CH=CH |
| Br | n-C$_3$H$_7$ | CH=CH |
| Br | n-C$_4$H$_9$ | CH=CH |
| Br | sec.-C$_4$H$_9$ | CH=CH |
| Br | i-C$_4$H$_9$ | CH=CH |
| Br | tert.-C$_4$H$_9$ | CH=CH |
| Br | n-C$_5$H$_{11}$ | CH=CH |
| Br | sec.-C$_5$H$_{11}$ | CH=CH |
| Br | n-C$_6$H$_{13}$ | CH=CH |
| Br | n-C$_7$H$_{15}$ | CH=CH |
| Br | sec.-C$_7$H$_{15}$ | CH=CH |
| Br | 1-Methylvinyl | CH=CH |
| Br | 2-Methylvinyl | CH=CH |
| Br | Allyl | CH=CH |
| Br | 2-Methylallyl | CH=CH |
| Br | 2-Ethylallyl | CH=CH |
| Br | 1-Methylallyl | CH=CH |
| Br | 1-Ethylallyl | CH=CH |
| Br | 1-Methyl-2-butenyl | CH=CH |
| Br | 1-Ethyl-2-butenyl | CH=CH |
| Br | Cyclopropyl | CH=CH |
| Br | Cyclobutyl | CH=CH |
| Br | Cyclopentyl | CH=CH |
| Br | Cyclohexyl | CH=CH |
| Br | 2-Cyclopentenyl | CH=CH |
| Br | 1-Cyclopentenyl | CH=CH |
| Br | 2-Cyclohexenyl | CH=CH |
| Br | 1-Cyclohexenyl | CH=CH |
| Br | Phenyl | CH=CH |

TABLE B

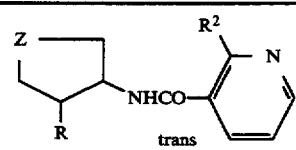

I.2

| R² | R | Z |
|---|---|---|
| Cl | C$_2$H$_5$ | CH$_2$CH$_2$ |
| Cl | i-C$_3$H$_7$ | CH$_2$CH$_2$ |
| Cl | n-C$_3$H$_7$ | CH$_2$CH$_2$ |
| Cl | n-C$_4$H$_9$ | CH$_2$CH$_2$ |
| Cl | sec.-C$_4$H$_9$ | CH$_2$CH$_2$ |
| Cl | i-C$_4$H$_9$ | CH$_2$CH$_2$ |
| Cl | tert.-C$_4$H$_9$ | CH$_2$CH$_2$ |
| Cl | n-C$_5$H$_{11}$ | CH$_2$CH$_2$ |
| Cl | sec.-C$_5$H$_{11}$ | CH$_2$CH$_2$ |
| Cl | n-C$_6$H$_{13}$ | CH$_2$CH$_2$ |
| Cl | n-C$_7$H$_{15}$ | CH$_2$CH$_2$ |
| Cl | sec.-C$_7$H$_{15}$ | CH$_2$CH$_2$ |
| Cl | 1-Methylvinyl | CH$_2$CH$_2$ |
| Cl | 2-Methylvinyl | CH$_2$CH$_2$ |
| Cl | Allyl | CH$_2$CH$_2$ |
| Cl | 2-Methylallyl | CH$_2$CH$_2$ |
| Cl | 2-Ethylallyl | CH$_2$CH$_2$ |
| Cl | 1-Methylallyl | CH$_2$CH$_2$ |
| Cl | 1-Ethylallyl | CH$_2$CH$_2$ |
| Cl | 1-Methyl-2-butenyl | CH$_2$CH$_2$ |
| Cl | 1-Ethyl-2-butenyl | CH$_2$CH$_2$ |
| Cl | Cyclopropyl | CH$_2$CH$_2$ |
| Cl | Cyclobutyl | CH$_2$CH$_2$ |
| Cl | Cyclopentyl | CH$_2$CH$_2$ |
| Cl | Cyclohexyl | CH$_2$CH$_2$ |
| Cl | 2-Cyclopentenyl | CH$_2$CH$_2$ |
| Cl | 1-Cyclopentenyl | CH$_2$CH$_2$ |
| Cl | 2-Cyclohexenyl | CH$_2$CH$_2$ |
| Cl | 1-Cyclohexenyl | CH$_2$CH$_2$ |
| Cl | Phenyl | CH$_2$CH$_2$ |
| Cl | C$_2$H$_5$ | CH=CH |

TABLE B-continued

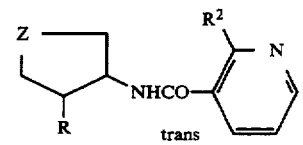

I.2

| R² | R | Z |
|---|---|---|
| Cl | i-C$_3$H$_7$ | CH=CH |
| Cl | n-C$_3$H$_7$ | CH=CH |
| Cl | n-C$_4$H$_9$ | CH=CH |
| Cl | sec.-C$_4$H$_9$ | CH=CH |
| Cl | i-C$_4$H$_9$ | CH=CH |
| Cl | tert.-C$_4$H$_9$ | CH=CH |
| Cl | n-C$_5$H$_{11}$ | CH=CH |
| Cl | sec.-C$_5$H$_{11}$ | CH=CH |
| Cl | n-C$_6$H$_{13}$ | CH=CH |
| Cl | n-C$_7$H$_{15}$ | CH=CH |
| Cl | sec.-C$_7$H$_{15}$ | CH=CH |
| Cl | 1-Methylvinyl | CH=CH |
| Cl | 2-Methylvinyl | CH=CH |
| Cl | Allyl | CH=CH |
| Cl | 2-Methylallyl | CH=CH |
| Cl | 2-Ethylallyl | CH=CH |
| Cl | 1-Methylallyl | CH=CH |
| Cl | 1-Ethylallyl | CH=CH |
| Cl | 1-Methyl-2-butenyl | CH=CH |
| Cl | 1-Ethyl-2-butenyl | CH=CH |
| Cl | Cyclopropyl | CH=CH |
| Cl | Cyclobutyl | CH=CH |
| Cl | Cyclopentyl | CH=CH |
| Cl | Cyclohexyl | CH=CH |
| Cl | 2-Cyclopentenyl | CH=CH |
| Cl | 1-Cyclopentenyl | CH=CH |
| Cl | 2-Cyclohexenyl | CH=CH |
| Cl | 1-Cyclohexenyl | CH=CH |
| Cl | Phenyl | CH=CH |

TABLE C

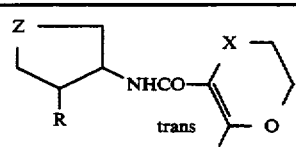

I.3

| X | R | Z |
|---|---|---|
| CH$_2$ | C$_2$H$_5$ | CH$_2$CH$_2$ |
| CH$_2$ | i-C$_3$H$_7$ | CH$_2$CH$_2$ |
| CH$_2$ | n-C$_3$H$_7$ | CH$_2$CH$_2$ |
| CH$_2$ | n-C$_4$H$_9$ | CH$_2$CH$_2$ |
| CH$_2$ | sec.-C$_4$H$_9$ | CH$_2$CH$_2$ |
| CH$_2$ | i-C$_4$H$_9$ | CH$_2$CH$_2$ |
| CH$_2$ | tert.-C$_4$H$_9$ | CH$_2$CH$_2$ |
| CH$_2$ | n-C$_5$H$_{11}$ | CH$_2$CH$_2$ |
| CH$_2$ | sec.-C$_5$H$_{11}$ | CH$_2$CH$_2$ |
| CH$_2$ | n-C$_6$H$_{13}$ | CH$_2$CH$_2$ |
| CH$_2$ | n-C$_7$H$_{15}$ | CH$_2$CH$_2$ |
| CH$_2$ | sec.-C$_7$H$_{15}$ | CH$_2$CH$_2$ |
| CH$_2$ | 1-Methylvinyl | CH$_2$CH$_2$ |
| CH$_2$ | 2-Methylvinyl | CH$_2$CH$_2$ |
| CH$_2$ | Allyl | CH$_2$CH$_2$ |
| CH$_2$ | 2-Methylallyl | CH$_2$CH$_2$ |
| CH$_2$ | 2-Ethylallyl | CH$_2$CH$_2$ |
| CH$_2$ | 1-Methylallyl | CH$_2$CH$_2$ |
| CH$_2$ | 1-Ethylallyl | CH$_2$CH$_2$ |
| CH$_2$ | 1-Methyl-2-butenyl | CH$_2$CH$_2$ |
| CH$_2$ | 1-Ethyl-2-butenyl | CH$_2$CH$_2$ |
| CH$_2$ | Cyclopropyl | CH$_2$CH$_2$ |
| CH$_2$ | Cyclobutyl | CH$_2$CH$_2$ |
| CH$_2$ | Cyclopentyl | CH$_2$CH$_2$ |
| CH$_2$ | Cyclohexyl | CH$_2$CH$_2$ |
| CH$_2$ | 2-Cyclopentenyl | CH$_2$CH$_2$ |
| CH$_2$ | 1-Cyclopentenyl | CH$_2$CH$_2$ |
| CH$_2$ | 2-Cyclohexenyl | CH$_2$CH$_2$ |
| CH$_2$ | 1-Cyclohexenyl | CH$_2$CH$_2$ |
| CH$_2$ | Phenyl | CH$_2$CH$_2$ |

TABLE C-continued

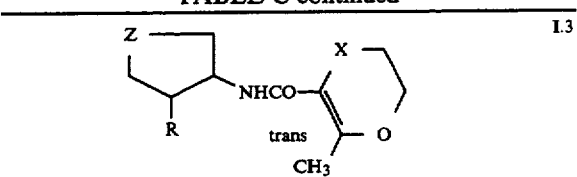

I.3

| X | R | Z |
|---|---|---|
| S | C$_2$H$_5$ | CH$_2$CH$_2$ |
| S | i-C$_3$H$_7$ | CH$_2$CH$_2$ |
| S | n-C$_3$H$_7$ | CH$_2$CH$_2$ |
| S | n-C$_4$H$_9$ | CH$_2$CH$_2$ |
| S | sec.-C$_4$H$_9$ | CH$_2$CH$_2$ |
| S | i-C$_4$H$_9$ | CH$_2$CH$_2$ |
| S | tert.-C$_4$H$_9$ | CH$_2$CH$_2$ |
| S | n-C$_5$H$_{11}$ | CH$_2$CH$_2$ |
| S | sec.-C$_5$H$_{11}$ | CH$_2$CH$_2$ |
| S | n-C$_6$H$_{13}$ | CH$_2$CH$_2$ |
| S | n-C$_7$H$_{15}$ | CH$_2$CH$_2$ |
| S | sec.-C$_7$H$_{15}$ | CH$_2$CH$_2$ |
| S | 1-Methylvinyl | CH$_2$CH$_2$ |
| S | 2-Methylvinyl | CH$_2$CH$_2$ |
| S | Allyl | CH$_2$CH$_2$ |
| S | 2-Methylallyl | CH$_2$CH$_2$ |
| S | 2-Ethylallyl | CH$_2$CH$_2$ |
| S | 1-Methylallyl | CH$_2$CH$_2$ |
| S | 1-Ethylallyl | CH$_2$CH$_2$ |
| S | 1-Methyl-2-butenyl | CH$_2$CH$_2$ |
| S | 1-Ethyl-2-butenyl | CH$_2$CH$_2$ |
| S | Cyclopropyl | CH$_2$CH$_2$ |
| S | Cyclobutyl | CH$_2$CH$_2$ |
| S | Cyclopentyl | CH$_2$CH$_2$ |
| S | Cyclohexyl | CH$_2$CH$_2$ |
| S | 2-Cyclopentenyl | CH$_2$CH$_2$ |
| S | 1-Cyclopentenyl | CH$_2$CH$_2$ |
| S | 2-Cyclohexenyl | CH$_2$CH$_2$ |
| S | 1-Cyclohexenyl | CH$_2$CH$_2$ |
| S | Phenyl | CH$_2$CH$_2$ |
| O | C$_2$H$_5$ | CH$_2$CH$_2$ |
| O | i-C$_3$H$_7$ | CH$_2$CH$_2$ |
| O | n-C$_3$H$_7$ | CH$_2$CH$_2$ |
| O | n-C$_4$H$_9$ | CH$_2$CH$_2$ |
| O | sec.-C$_4$H$_9$ | CH$_2$CH$_2$ |
| O | i-C$_4$H$_9$ | CH$_2$CH$_2$ |
| O | tert.-C$_4$H$_9$ | CH$_2$CH$_2$ |
| O | n-C$_5$H$_{11}$ | CH$_2$CH$_2$ |
| O | sec.-C$_5$H$_{11}$ | CH$_2$CH$_2$ |
| O | n-C$_6$H$_{13}$ | CH$_2$CH$_2$ |
| O | n-C$_7$H$_{15}$ | CH$_2$CH$_2$ |
| O | sec.-C$_7$H$_{15}$ | CH$_2$CH$_2$ |
| O | 1-Methylvinyl | CH$_2$CH$_2$ |
| O | 2-Methylvinyl | CH$_2$CH$_2$ |
| O | Allyl | CH$_2$CH$_2$ |
| O | 2-Methylallyl | CH$_2$CH$_2$ |
| O | 2-Ethylallyl | CH$_2$CH$_2$ |
| O | 1-Methylallyl | CH$_2$CH$_2$ |
| O | 1-Ethylallyl | CH$_2$CH$_2$ |
| O | 1-Methyl-2-butenyl | CH$_2$CH$_2$ |
| O | 1-Ethyl-2-butenyl | CH$_2$CH$_2$ |
| O | Cyclopropyl | CH$_2$CH$_2$ |
| O | Cyclobutyl | CH$_2$CH$_2$ |
| O | Cyclopentyl | CH$_2$CH$_2$ |
| O | Cyclohexyl | CH$_2$CH$_2$ |
| O | 2-Cyclopentenyl | CH$_2$CH$_2$ |
| O | 1-Cyclopentenyl | CH$_2$CH$_2$ |
| O | 2-Cyclohexenyl | CH$_2$CH$_2$ |
| O | 1-Cyclohexenyl | CH$_2$CH$_2$ |
| O | Phenyl | CH$_2$CH$_2$ |
| CH$_2$ | C$_2$H$_5$ | CH=CH |
| CH$_2$ | i-C$_3$H$_7$ | CH=CH |
| CH$_2$ | n-C$_3$H$_7$ | CH=CH |
| CH$_2$ | n-C$_4$H$_9$ | CH=CH |
| CH$_2$ | sec.-C$_4$H$_9$ | CH=CH |
| CH$_2$ | i-C$_4$H$_9$ | CH=CH |
| CH$_2$ | tert.-C$_4$H$_9$ | CH=CH |
| CH$_2$ | n-C$_5$H$_{11}$ | CH=CH |
| CH$_2$ | sec.-C$_5$H$_{11}$ | CH=CH |
| CH$_2$ | n-C$_6$H$_{13}$ | CH=CH |
| CH$_2$ | n-C$_7$H$_{15}$ | CH=CH |
| CH$_2$ | sec.-C$_7$H$_{15}$ | CH=CH |

TABLE C-continued

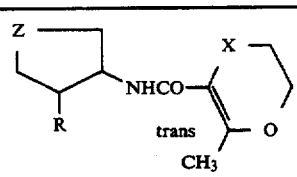

I.3

| X | R | Z |
|---|---|---|
| CH$_2$ | 1-Methylvinyl | CH=CH |
| CH$_2$ | 2-Methylvinyl | CH=CH |
| CH$_2$ | Allyl | CH=CH |
| CH$_2$ | 2-Methylallyl | CH=CH |
| CH$_2$ | 2-Ethylallyl | CH=CH |
| CH$_2$ | 1-Methylallyl | CH=CH |
| CH$_2$ | 1-Ethylallyl | CH=CH |
| CH$_2$ | 1-Methyl-2-butenyl | CH=CH |
| CH$_2$ | 1-Ethyl-2-butenyl | CH=CH |
| CH$_2$ | Cyclopropyl | CH=CH |
| CH$_2$ | Cyclobutyl | CH=CH |
| CH$_2$ | Cyclopentyl | CH=CH |
| CH$_2$ | Cyclohexyl | CH=CH |
| CH$_2$ | 2-Cyclopentenyl | CH=CH |
| CH$_2$ | 1-Cyclopentenyl | CH=CH |
| CH$_2$ | 2-Cyclohexenyl | CH=CH |
| CH$_2$ | 1-Cyclohexenyl | CH=CH |
| CH$_2$ | Phenyl | CH=CH |
| S | C$_2$H$_5$ | CH=CH |
| S | i-C$_3$H$_7$ | CH=CH |
| S | n-C$_3$H$_7$ | CH=CH |
| S | n-C$_4$H$_9$ | CH=CH |
| S | sec.-C$_4$H$_9$ | CH=CH |
| S | i-C$_4$H$_9$ | CH=CH |
| S | tert.-C$_4$H$_9$ | CH=CH |
| S | n-C$_5$H$_{11}$ | CH=CH |
| S | sec.-C$_5$H$_{11}$ | CH=CH |
| S | n-C$_6$H$_{13}$ | CH=CH |
| S | n-C$_7$H$_{15}$ | CH=CH |
| S | sec.-C$_7$H$_{15}$ | CH=CH |
| S | 1-Methylvinyl | CH=CH |
| S | 2-Methylvinyl | CH=CH |
| S | Allyl | CH=CH |
| S | 2-Methylallyl | CH=CH |
| S | 2-Ethylallyl | CH=CH |
| S | 1-Methylallyl | CH=CH |
| S | 1-Ethylallyl | CH=CH |
| S | 1-Methyl-2-butenyl | CH=CH |
| S | 1-Ethyl-2-butenyl | CH=CH |
| S | Cyclopropyl | CH=CH |
| S | Cyclobutyl | CH=CH |
| S | Cyclopentyl | CH=CH |
| S | Cyclohexyl | CH=CH |
| S | 2-Cyclopentenyl | CH=CH |
| S | 1-Cyclopentenyl | CH=CH |
| S | 2-Cyclohexenyl | CH=CH |
| S | 1-Cyclohexenyl | CH=CH |
| S | Phenyl | CH=CH |
| O | C$_2$H$_5$ | CH=CH |
| O | i-C$_3$H$_7$ | CH=CH |
| O | n-C$_3$H$_7$ | CH=CH |
| O | n-C$_4$H$_9$ | CH=CH |
| O | sec.-C$_4$H$_9$ | CH=CH |
| O | i-C$_4$H$_9$ | CH=CH |
| O | tert.-C$_4$H$_9$ | CH=CH |
| O | n-C$_5$H$_{11}$ | CH=CH |
| O | sec.-C$_5$H$_{11}$ | CH=CH |
| O | n-C$_6$H$_{13}$ | CH=CH |
| O | n-C$_7$H$_{15}$ | CH=CH |
| O | sec.-C$_7$H$_{15}$ | CH=CH |
| O | 1-Methylvinyl | CH=CH |
| O | 2-Methylvinyl | CH=CH |
| O | Allyl | CH=CH |
| O | 2-Methylallyl | CH=CH |
| O | 2-Ethylallyl | CH=CH |
| O | 1-Methylallyl | CH=CH |
| O | 1-Ethylallyl | CH=CH |
| O | 1-Methyl-2-butenyl | CH=CH |
| O | 1-Ethyl-2-butenyl | CH=CH |
| O | Cyclopropyl | CH=CH |
| O | Cyclobutyl | CH=CH |
| O | Cyclopentyl | CH=CH |

TABLE C-continued

I.3

Structure: Z-CH2-CH(-)-CH(R)- with NHCO-C(=C(CH3)-O-)-X-CH2-CH2 (trans), 6-membered ring

| X | R | Z |
|---|---|---|
| O | Cyclohexyl | CH=CH |
| O | 2-Cyclopentenyl | CH=CH |
| O | 1-Cyclopentenyl | CH=CH |
| O | 2-Cyclohexenyl | CH=CH |
| O | 1-Cyclohexenyl | CH=CH |
| O | Phenyl | CH=CH |

TABLE D

I.4

Structure: Z-CH2-CH(-)-CH(R)-NHCO-C(=C(CH3)-Y-CH2-CH2) (trans), 5-membered ring

| R | Y | Z |
|---|---|---|
| C2H5 | S | CH2CH2 |
| i-C3H7 | S | CH2CH2 |
| n-C3H7 | S | CH2CH2 |
| n-C4H9 | S | CH2CH2 |
| sec.-C4H9 | S | CH2CH2 |
| i-C4H9 | S | CH2CH2 |
| tert.-C4H9 | S | CH2CH2 |
| n-C5H11 | S | CH2CH2 |
| sec.-C5H11 | S | CH2CH2 |
| n-C6H13 | S | CH2CH2 |
| n-C7H15 | S | CH2CH2 |
| sec.-C7H15 | S | CH2CH2 |
| 1-Methylvinyl | S | CH2CH2 |
| 2-Methylvinyl | S | CH2CH2 |
| Allyl | S | CH2CH2 |
| 2-Methylallyl | S | CH2CH2 |
| 2-Ethylallyl | S | CH2CH2 |
| 1-Methylallyl | S | CH2CH2 |
| l-Ethylallyl | S | CH2CH2 |
| 1-Methyl-2-butenyl | S | CH2CH2 |
| l-Ethyl-2-butenyl | S | CH2CH2 |
| Cyclopropyl | S | CH2CH2 |
| Cyclobutyl | S | CH2CH2 |
| Cyclopentyl | S | CH2CH2 |
| Cyclohexyl | S | CH2CH2 |
| 2-Cyclopentenyl | S | CH2CH2 |
| 1-Cyclopentenyl | S | CH2CH2 |
| 2-Cyclohexenyl | S | CH2CH2 |
| 1-Cyclohexenyl | S | CH2CH2 |
| Phenyl | S | CH2CH2 |
| C2H5 | O | CH2CH2 |
| i-C3H7 | O | CH2CH2 |
| n-C3H7 | O | CH2CH2 |
| n-C4H9 | O | CH2CH2 |
| sec.-C4H9 | O | CH2CH2 |
| i-C4H9 | O | CH2CH2 |
| tert.-C4H9 | O | CH2CH2 |
| n-C5H11 | O | CH2CH2 |
| sec.-C5H11 | O | CH2CH2 |
| n-C6H13 | O | CH2CH2 |
| n-C7H15 | O | CH2CH2 |
| sec.-C7H15 | O | CH2CH2 |
| 1-Methylvinyl | O | CH2CH2 |
| 2-Methylvinyl | O | CH2CH2 |
| Allyl | O | CH2CH2 |
| 2-Methylallyl | O | CH2CH2 |
| 2-Ethylallyl | O | CH2CH2 |
| 1-Methylallyl | O | CH2CH2 |
| l-Ethylallyl | O | CH2CH2 |
| 1-Methyl-2-butenyl | O | CH2CH2 |
| l-Ethyl-2-butenyl | O | CH2CH2 |
| Cyclopropyl | O | CH2CH2 |
| Cyclobutyl | O | CH2CH2 |
| Cyclopentyl | O | CH2CH2 |

TABLE D-continued

I.4

| R | Y | Z |
|---|---|---|
| Cyclohexyl | O | CH2CH2 |
| 2-Cyclopentenyl | O | CH2CH2 |
| 1-Cyclopentenyl | O | CH2CH2 |
| 2-Cyclohexenyl | O | CH2CH2 |
| 1-Cyclohexenyl | O | CH2CH2 |
| Phenyl | O | CH2CH2 |
| C2H5 | S | CH=CH |
| i-C3H7 | S | CH=CH |
| n-C3H7 | S | CH=CH |
| n-C4H9 | S | CH=CH |
| sec.-C4H9 | S | CH=CH |
| i-C4H9 | S | CH=CH |
| tert.-C4H9 | S | CH=CH |
| n-C5H11 | S | CH=CH |
| sec.-C5H11 | S | CH=CH |
| n-C6H13 | S | CH=CH |
| n-C7H15 | S | CH=CH |
| sec.-C7H15 | S | CH=CH |
| 1-Methylvinyl | S | CH=CH |
| 2-Methylvinyl | S | CH=CH |
| Allyl | S | CH=CH |
| 2-Methylallyl | S | CH=CH |
| 2-Ethylallyl | S | CH=CH |
| 1-Methylallyl | S | CH=CH |
| l-Ethylallyl | S | CH=CH |
| 1-Methyl-2-butenyl | S | CH=CH |
| l-Ethyl-2-butenyl | S | CH=CH |
| Cyclopropyl | S | CH=CH |
| Cyclobutyl | S | CH=CH |
| Cyclopentyl | S | CH=CH |
| Cyclohexyl | S | CH=CH |
| 2-Cyclopentenyl | S | CH=CH |
| 1-Cyclopentenyl | S | CH=CH |
| 2-Cyclohexenyl | S | CH=CH |
| 1-Cyclohexenyl | S | CH=CH |
| Phenyl | S | CH=CH |
| C2H5 | O | CH=CH |
| i-C3H7 | O | CH=CH |
| n-C3H7 | O | CH=CH |
| n-C4H9 | O | CH=CH |
| sec.-C4H9 | O | CH=CH |
| i-C4H9 | O | CH=CH |
| tert.-C4H9 | O | CH=CH |
| n-C5H11 | O | CH=CH |
| sec.-C5H11 | O | CH=CH |
| n-C6H13 | O | CH=CH |
| n-C7H15 | O | CH=CH |
| sec.-C7H15 | O | CH=CH |
| 1-Methylvinyl | O | CH=CH |
| 2-Methylvinyl | O | CH=CH |
| Allyl | O | CH=CH |
| 2-Methylallyl | O | CH=CH |
| 2-Ethylallyl | O | CH=CH |
| 1-Methylallyl | O | CH=CH |
| l-Ethylallyl | O | CH=CH |
| 1-Methyl-2-butenyl | O | CH=CH |
| l-Ethyl-2-butenyl | O | CH=CH |
| Cyclopropyl | O | CH=CH |
| Cyclobutyl | O | CH=CH |
| Cyclopentyl | O | CH=CH |
| Cyclohexyl | O | CH=CH |
| 2-Cyclopentenyl | O | CH=CH |
| 1-Cyclopentenyl | O | CH=CH |
| 2-Cyclohexenyl | O | CH=CH |
| 1-Cyclohexenyl | O | CH=CH |
| Phenyl | O | CH=CH |

TABLE E

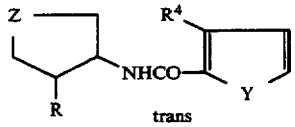

I.5 trans

| R⁴ | R | Y | Z |
|---|---|---|---|
| CH₃ | i-C₃H₇ | O | CH₂CH₂ |
| CH₃ | n-C₃H₇ | O | CH₂CH₂ |
| CH₃ | n-C₄H₉ | O | CH₂CH₂ |
| CH₃ | sec.-C₄H₉ | O | CH₂CH₂ |
| CH₃ | i-C₄H₉ | O | CH₂CH₂ |
| CH₃ | tert.-C₄H₉ | O | CH₂CH₂ |
| CH₃ | n-C₅H₁₁ | O | CH₂CH₂ |
| CH₃ | sec.-C₅H₁₁ | O | CH₂CH₂ |
| CH₃ | n-C₆H₁₃ | O | CH₂CH₂ |
| CH₃ | n-C₇H₁₅ | O | CH₂CH₂ |
| CH₃ | sec.-C₇H₁₅ | O | CH₂CH₂ |
| CH₃ | Ethoxy | O | CH₂CH₂ |
| CH₃ | Propoxy | O | CH₂CH₂ |
| CH₃ | 1-Methylethoxy | O | CH₂CH₂ |
| CH₃ | n-Butoxy | O | CH₂CH₂ |
| CH₃ | 1-Methylpropoxy | O | CH₂CH₂ |
| CH₃ | 2-Methylpropoxy | O | CH₂CH₂ |
| CH₃ | 1,1-Dimethylethoxy | O | CH₂CH₂ |
| CH₃ | n-Pentyloxy | O | CH₂CH₂ |
| CH₃ | n-Hexyloxy | O | CH₂CH₂ |
| CH₃ | Cyclopentyl | O | CH₂CH₂ |
| CH₃ | Cyclopentenyl | O | CH₂CH₂ |
| CH₃ | i-C₃H₇ | S | CH₂CH₂ |
| CH₃ | n-C₃H₇ | S | CH₂CH₂ |
| CH₃ | n-C₄H₉ | S | CH₂CH₂ |
| CH₃ | sec.-C₄H₉ | S | CH₂CH₂ |
| CH₃ | i-C₄H₉ | S | CH₂CH₂ |
| CH₃ | tert.-C₄H₉ | S | CH₂CH₂ |
| CH₃ | n-C₅H₁₁ | S | CH₂CH₂ |
| CH₃ | sec.-C₅H₁₁ | S | CH₂CH₂ |
| CH₃ | n-C₆H₁₃ | S | CH₂CH₂ |
| CH₃ | n-C₇H₁₅ | S | CH₂CH₂ |
| CH₃ | sec.-C₇H₁₅ | S | CH₂CH₂ |
| CH₃ | Ethoxy | S | CH₂CH₂ |
| CH₃ | Propoxy | S | CH₂CH₂ |
| CH₃ | 1-Methylethoxy | S | CH₂CH₂ |
| CH₃ | n-Butoxy | S | CH₂CH₂ |
| CH₃ | 1-Methylpropoxy | S | CH₂CH₂ |
| CH₃ | 2-Methylpropoxy | S | CH₂CH₂ |
| CH₃ | 1,1-Dimethylethoxy | S | CH₂CH₂ |
| CH₃ | n-Pentyloxy | S | CH₂CH₂ |
| CH₃ | n-Hexyloxy | S | CH₂CH₂ |
| CH₃ | Cyclopentyl | S | CH₂CH₂ |
| CH₃ | Cyclopentenyl | S | CH₂CH₂ |
| CH₃ | i-C₃H₇ | O | CH=CH |
| CH₃ | n-C₃H₇ | O | CH=CH |
| CH₃ | n-C₄H₉ | O | CH=CH |
| CH₃ | sec.-C₄H₉ | O | CH=CH |
| CH₃ | i-C₄H₉ | O | CH=CH |
| CH₃ | tert.-C₄H₉ | O | CH=CH |
| CH₃ | n-C₅H₁₁ | O | CH=CH |
| CH₃ | sec.-C₅H₁₁ | O | CH=CH |
| CH₃ | n-C₆H₁₃ | O | CH=CH |
| CH₃ | n-C₇H₁₅ | O | CH=CH |
| CH₃ | sec.-C₇H₁₅ | O | CH=CH |
| CH₃ | Ethoxy | O | CH=CH |
| CH₃ | Propoxy | O | CH=CH |
| CH₃ | 1-Methylethoxy | O | CH=CH |
| CH₃ | n-Butoxy | O | CH=CH |
| CH₃ | 1-Methylpropoxy | O | CH=CH |
| CH₃ | 2-Methylpropoxy | O | CH=CH |
| CH₃ | 1,1-Dimethylethoxy | O | CH=CH |
| CH₃ | n-Pentyloxy | O | CH=CH |
| CH₃ | n-Hexyloxy | O | CH=CH |
| CH₃ | Cyclopentyl | O | CH=CH |
| CH₃ | Cyclopentenyl | O | CH=CH |
| CH₃ | i-C₃H₇ | S | CH=CH |
| CH₃ | n-C₃H₇ | S | CH=CH |
| CH₃ | n-C₄H₉ | S | CH=CH |
| CH₃ | sec.-C₄H₉ | S | CH=CH |
| CH₃ | i-C₄H₉ | S | CH=CH |
| CH₃ | tert.-C₄H₉ | S | CH=CH |
| CH₃ | n-C₅H₁₁ | S | CH=CH |
| CH₃ | sec.-C₅H₁₁ | S | CH=CH |

TABLE E-continued

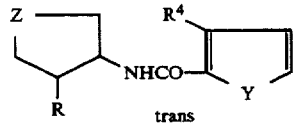

I.5 trans

| R⁴ | R | Y | Z |
|---|---|---|---|
| CH₃ | n-C₆H₁₃ | S | CH=CH |
| CH₃ | n-C₇H₁₅ | S | CH=CH |
| CH₃ | sec.-C₇H₁₅ | S | CH=CH |
| CH₃ | Ethoxy | S | CH=CH |
| CH₃ | Propoxy | S | CH=CH |
| CH₃ | 1-Methylethoxy | S | CH=CH |
| CH₃ | n-Butoxy | S | CH=CH |
| CH₃ | 1-Methylpropoxy | S | CH=CH |
| CH₃ | 2-Methylpropoxy | S | CH=CH |
| CH₃ | 1,1-Dimethylethoxy | S | CH=CH |
| CH₃ | n-Pentyloxy | S | CH=CH |
| CH₃ | n-Hexyloxy | S | CH=CH |
| CH₃ | Cyclopentyl | S | CH=CH |
| CH₃ | Cyclopentenyl | S | CH=CH |

TABLE F

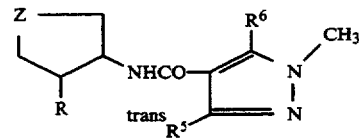

trans

| R⁵ | R⁶ | R | Z |
|---|---|---|---|
| CH₃ | H | C₂H₅ | CH₂CH₂ |
| CH₃ | H | i-C₃H₇ | CH₂CH₂ |
| CH₃ | H | n-C₃H₇ | CH₂CH₂ |
| CH₃ | H | n-C₄H₉ | CH₂CH₂ |
| CH₃ | H | sec.-C₄H₉ | CH₂CH₂ |
| CH₃ | H | i-C₄H₉ | CH₂CH₂ |
| CH₃ | H | tert.-C₄H₉ | CH₂CH₂ |
| CH₃ | H | n-C₅H₁₁ | CH₂CH₂ |
| CH₃ | H | sec.-C₅H₁₁ | CH₂CH₂ |
| CH₃ | H | n-C₆H₁₃ | CH₂CH₂ |
| CH₃ | H | n-C₇H₁₅ | CH₂CH₂ |
| CH₃ | H | sec.-C₇H₁₅ | CH₂CH₂ |
| CH₃ | H | 1-Methylvinyl | CH₂CH₂ |
| CH₃ | H | 2-Methylvinyl | CH₂CH₂ |
| CH₃ | H | Allyl | CH₂CH₂ |
| CH₃ | H | 2-Methylallyl | CH₂CH₂ |
| CH₃ | H | 2-Ethylallyl | CH₂CH₂ |
| CH₃ | H | 1-Methylallyl | CH₂CH₂ |
| CH₃ | H | 1-Ethylallyl | CH₂CH₂ |
| CH₃ | H | 1-Methyl-2-butenyl | CH₂CH₂ |
| CH₃ | H | 1-Ethyl-2-butenyl | CH₂CH₂ |
| CH₃ | H | Cyclopropyl | CH₂CH₂ |
| CH₃ | H | Cyclobutyl | CH₂CH₂ |
| CH₃ | H | Cyclopentyl | CH₂CH₂ |
| CH₃ | H | Cyclohexyl | CH₂CH₂ |
| CH₃ | H | 2-Cyclopentenyl | CH₂CH₂ |
| CH₃ | H | 1-Cyclopentenyl | CH₂CH₂ |
| CH₃ | H | 2-Cyclohexenyl | CH₂CH₂ |
| CH₃ | H | 1-Cyclohexenyl | CH₂CH₂ |
| CH₃ | H | Phenyl | CH₂CH₂ |
| CF₃ | H | C₂H₅ | CH₂CH₂ |
| CF₃ | H | i-C₃H₇ | CH₂CH₂ |
| CF₃ | H | n-C₃H₇ | CH₂CH₂ |
| CF₃ | H | n-C₄H₉ | CH₂CH₂ |
| CF₃ | H | sec.-C₄H₉ | CH₂CH₂ |
| CF₃ | H | i-C₄H₉ | CH₂CH₂ |
| CF₃ | H | tert.-C₄H₉ | CH₂CH₂ |
| CF₃ | H | n-C₅H₁₁ | CH₂CH₂ |
| CF₃ | H | sec.-C₅H₁₁ | CH₂CH₂ |
| CF₃ | H | n-C₆H₁₃ | CH₂CH₂ |
| CF₃ | H | n-C₇H₁₅ | CH₂CH₂ |
| CF₃ | H | sec.-C₇H₁₅ | CH₂CH₂ |
| CF₃ | H | 1-Methylvinyl | CH₂CH₂ |
| CF₃ | H | 2-Methylvinyl | CH₂CH₂ |
| CF₃ | H | Allyl | CH₂CH₂ |
| CF₃ | H | 2-Methylallyl | CH₂CH₂ |

TABLE F-continued

Structure: Z—[ring with R substituent]—NHCO—C(R⁶)=C(R⁵)—N(CH₃)—N, trans

| R⁵ | R⁶ | R | Z |
|---|---|---|---|
| CF₃ | H | 2-Ethylallyl | CH₂CH₂ |
| CF₃ | H | 1-Methylallyl | CH₂CH₂ |
| CF₃ | H | l-Ethylallyl | CH₂CH₂ |
| CF₃ | H | 1-Methyl-2-butenyl | CH₂CH₂ |
| CF₃ | H | l-Ethyl-2-butenyl | CH₂CH₂ |
| CF₃ | H | Cyclopropyl | CH₂CH₂ |
| CF₃ | H | Cyclobutyl | CH₂CH₂ |
| CF₃ | H | Cyclopentyl | CH₂CH₂ |
| CF₃ | H | Cyclohexyl | CH₂CH₂ |
| CF₃ | H | 2-Cyclopentenyl | CH₂CH₂ |
| CF₃ | H | 1-Cyclopentenyl | CH₂CH₂ |
| CF₃ | H | 2-Cyclohexenyl | CH₂CH₂ |
| CF₃ | H | 1-Cyclohexenyl | CH₂CH₂ |
| CF₃ | H | Phenyl | CH₂CH₂ |
| CH₃ | H | C₂H₅ | CH=CH |
| CH₃ | H | i-C₃H₇ | CH=CH |
| CH₃ | H | n-C₃H₇ | CH=CH |
| CH₃ | H | n-C₄H₉ | CH=CH |
| CH₃ | H | sec.-C₄H₉ | CH=CH |
| CH₃ | H | i-C₄H₉ | CH=CH |
| CH₃ | H | tert.-C₄H₉ | CH=CH |
| CH₃ | H | n-C₅H₁₁ | CH=CH |
| CH₃ | H | sec.-C₅H₁₁ | CH=CH |
| CH₃ | H | n-C₆H₁₃ | CH=CH |
| CH₃ | H | n-C₇H₁₅ | CH=CH |
| CH₃ | H | sec.-C₇H₁₅ | CH=CH |
| CH₃ | H | 1-Methylvinyl | CH=CH |
| CH₃ | H | 2-Methylvinyl | CH=CH |
| CH₃ | H | Allyl | CH=CH |
| CH₃ | H | 2-Methylallyl | CH=CH |
| CH₃ | H | 2-Ethylallyl | CH=CH |
| CH₃ | H | 1-Methylallyl | CH=CH |
| CH₃ | H | l-Ethylallyl | CH=CH |
| CH₃ | H | 1-Methyl-2-butenyl | CH=CH |
| CH₃ | H | l-Ethyl-2-butenyl | CH=CH |
| CH₃ | H | Cyclopropyl | CH=CH |
| CH₃ | H | Cyclobutyl | CH=CH |
| CH₃ | H | Cyclopentyl | CH=CH |
| CH₃ | H | Cyclohexyl | CH=CH |
| CH₃ | H | 2-Cyclopentenyl | CH=CH |
| CH₃ | H | 1-Cyclopentenyl | CH=CH |
| CH₃ | H | 2-Cyclohexenyl | CH=CH |
| CH₃ | H | 1-Cyclohexenyl | CH=CH |
| CH₃ | H | Phenyl | CH=CH |
| CF₃ | H | C₂H₅ | CH=CH |
| CF₃ | R | i-C₃H₇ | CH=CH |
| CF₃ | H | n-C₃H₇ | CH=CH |
| CF₃ | H | n-C₄H₉ | CH=CH |
| CF₃ | H | sec.-C₄H₉ | CH=CH |
| CF₃ | H | i-C₄H₉ | CH=CH |
| CF₃ | H | tert.-C₄H₉ | CH=CH |
| CF₃ | H | n-C₅H₁₁ | CH=CH |
| CF₃ | H | sec.-C₅H₁₁ | CH=CH |
| CF₃ | H | n-C₆H₁₃ | CH=CH |
| CF₃ | H | n-C₇H₁₅ | CH=CH |
| CF₃ | H | sec.-C₇H₁₅ | CH=CH |
| CF₃ | H | 1-Methylvinyl | CH=CH |
| CF₃ | H | 2-Methylvinyl | CH=CH |
| CF₃ | H | Allyl | CH=CH |
| CF₃ | H | 2-Methylallyl | CH=CH |
| CF₃ | H | 2-Ethylallyl | CH=CH |
| CF₃ | H | 1-Methylallyl | CH=CH |
| CF₃ | H | l-Ethylallyl | CH=CH |
| CF₃ | H | 1-Methyl-2-butenyl | CH=CH |
| CF₃ | H | l-Ethyl-2-butenyl | CH=CH |
| CF₃ | H | Cyclopropyl | CH=CH |
| CF₃ | H | Cyclobutyl | CH=CH |
| CF₃ | H | Cyclopentyl | CH=CH |
| CF₃ | H | Cyclohexyl | CH=CH |
| CF₃ | H | 2-Cyclopentenyl | CH=CH |
| CF₃ | H | 1-Cyclopentenyl | CH=CH |
| CF₃ | H | 2-Cyclohexenyl | CH=CH |
| CF₃ | H | 1-Cyclohexenyl | CH=CH |
| CF₃ | H | Phenyl | CH=CH |

TABLE G

Structure: Z—[ring with R substituent]—NHCO—C=C(R⁷)—S—C(R⁶)=N, trans (I.7)

| R⁷ | R⁶ | R | Z |
|---|---|---|---|
| CF₃ | CH₃ | C₂H₅ | CH₂CH₂ |
| CF₃ | CH₃ | i-C₃H₇ | CH₂CH₂ |
| CF₃ | CH₃ | n-C₃H₇ | CH₂CH₂ |
| CF₃ | CH₃ | n-C₄H₉ | CH₂CH₂ |
| CF₃ | CH₃ | sec.-C₄H₉ | CH₂CH₂ |
| CF₃ | CH₃ | i-C₄H₉ | CH₂CH₂ |
| CF₃ | CH₃ | tert.-C₄H₉ | CH₂CH₂ |
| CF₃ | CH₃ | n-C₅H₁₁ | CH₂CH₂ |
| CF₃ | CH₃ | sec.-C₅H₁₁ | CH₂CH₂ |
| CF₃ | CH₃ | n-C₆H₁₃ | CH₂CH₂ |
| CF₃ | CH₃ | n-C₇H₁₅ | CH₂CH₂ |
| CF₃ | CH₃ | sec.-C₇H₁₅ | CH₂CH₂ |
| CF₃ | CH₃ | 1-Methylvinyl | CH₂CH₂ |
| CF₃ | CH₃ | 2-Methylvinyl | CH₂CH₂ |
| CF₃ | CH₃ | Allyl | CH₂CH₂ |
| CF₃ | CH₃ | 2-Methylallyl | CH₂CH₂ |
| CF₃ | CH₃ | 2-Ethylallyl | CH₂CH₂ |
| CF₃ | CH₃ | 1-Methylallyl | CH₂CH₂ |
| CF₃ | CH₃ | l-Ethylallyl | CH₂CH₂ |
| CF₃ | CH₃ | 1-Methyl-2-butenyl | CH₂CH₂ |
| CF₃ | CH₃ | l-Ethyl-2-butenyl | CH₂CH₂ |
| CF₃ | CH₃ | Cyclopropyl | CH₂CH₂ |
| CF₃ | CH₃ | Cyclobutyl | CH₂CH₂ |
| CF₃ | CH₃ | Cyclopentyl | CH₂CH₂ |
| CF₃ | CH₃ | Cyclohexyl | CH₂CH₂ |
| CF₃ | CH₃ | 2-Cyclopentenyl | CH₂CH₂ |
| CF₃ | CH₃ | 1-Cyclopentenyl | CH₂CH₂ |
| CF₃ | CH₃ | 2-Cyclohexenyl | CH₂CH₂ |
| CF₃ | CH₃ | 1-Cyclohexenyl | CH₂CH₂ |
| CF₃ | CH₃ | Phenyl | CH₂CH₂ |
| CH₃ | CH₃ | C₂H₅ | CH₂CH₂ |
| CH₃ | CH₃ | i-C₃H₇ | CH₂CH₂ |
| CH₃ | CH₃ | n-C₃H₇ | CH₂CH₂ |
| CH₃ | CH₃ | n-C₄H₉ | CH₂CH₂ |
| CH₃ | CH₃ | sec.-C₄H₉ | CH₂CH₂ |
| CH₃ | CH₃ | i-C₄H₉ | CH₂CH₂ |
| CH₃ | CH₃ | tert.-C₄H₉ | CH₂CH₂ |
| CH₃ | CH₃ | n-C₅H₁₁ | CH₂CH₂ |
| CH₃ | CH₃ | sec.-C₅H₁₁ | CH₂CH₂ |
| CH₃ | CH₃ | n-C₆H₁₃ | CH₂CH₂ |
| CH₃ | CH₃ | n-C₇H₁₅ | CH₂CH₂ |
| CH₃ | CH₃ | sec.-C₇H₁₅ | CH₂CH₂ |
| CH₃ | CH₃ | 1-Methylvinyl | CH₂CH₂ |
| CH₃ | CH₃ | 2-Methylvinyl | CH₂CH₂ |
| CH₃ | CH₃ | Allyl | CH₂CH₂ |
| CH₃ | CH₃ | 2-Methylallyl | CH₂CH₂ |
| CH₃ | CH₃ | 2-Ethylallyl | CH₂CH₂ |
| CH₃ | CH₃ | 1-Methylallyl | CH₂CH₂ |
| CH₃ | CH₃ | l-Ethylallyl | CH₂CH₂ |
| CH₃ | CH₃ | 1-Methyl-2-butenyl | CH₂CH₂ |
| CH₃ | CH₃ | l-Ethyl-2-butenyl | CH₂CH₂ |
| CH₃ | CH₃ | Cyclopropyl | CH₂CH₂ |
| CH₃ | CH₃ | Cyclobutyl | CH₂CH₂ |
| CH₃ | CH₃ | Cyclopentyl | CH₂CH₂ |
| CH₃ | CH₃ | Cyclohexyl | CH₂CH₂ |
| CH₃ | CH₃ | 2-Cyclopentenyl | CH₂CH₂ |
| CH₃ | CH₃ | 1-Cyclopentenyl | CH₂CH₂ |
| CH₃ | CH₃ | 2-Cyclohexenyl | CH₂CH₂ |
| CH₃ | CH₃ | 1-Cyclohexenyl | CH₂CH₂ |

TABLE G-continued $$\underset{\text{trans}}{\overset{Z}{\underset{R}{\bigg|}}\overset{R^7}{\underset{NHCO}{\bigg\langle}}\overset{}{\underset{S}{\bigg\rangle}}\overset{N}{\underset{R^6}{\bigg|}}}$$

I.7

| $R^7$ | $R^6$ | R | Z |
|---|---|---|---|
| CH$_3$ | CH$_3$ | Phenyl | CH$_2$CH$_2$ |
| CF$_3$ | CH$_3$ | C$_2$H$_5$ | CH=CH |
| CF$_3$ | CH$_3$ | i-C$_3$H$_7$ | CH=CH |
| CF$_3$ | CH$_3$ | n-C$_3$H$_7$ | CH=CH |
| CF$_3$ | CH$_3$ | n-C$_4$H$_9$ | CH=CH |
| CF$_3$ | CH$_3$ | sec.-C$_4$H$_9$ | CH=CH |
| CF$_3$ | CH$_3$ | i-C$_4$H$_9$ | CH=CH |
| CF$_3$ | CH$_3$ | tert.-C$_4$H$_9$ | CH=CH |
| CF$_3$ | CH$_3$ | n-C$_5$H$_{11}$ | CH=CH |
| CF$_3$ | CH$_3$ | sec.-C$_5$H$_{11}$ | CH=CH |
| CF$_3$ | CH$_3$ | n-C$_6$H$_{13}$ | CH=CH |
| CF$_3$ | CH$_3$ | n-C$_7$H$_{15}$ | CH=CH |
| CF$_3$ | CH$_3$ | sec.-C$_7$H$_{15}$ | CH=CH |
| CF$_3$ | CH$_3$ | 1-Methylvinyl | CH=CH |
| CF$_3$ | CH$_3$ | 2-Methylvinyl | CH=CH |
| CF$_3$ | CH$_3$ | Allyl | CH=CH |
| CF$_3$ | CH$_3$ | 2-Methylallyl | CH=CH |
| CF$_3$ | CH$_3$ | 2-Ethylallyl | CH=CH |
| CF$_3$ | CH$_3$ | 1-Methylallyl | CH=CH |
| CF$_3$ | CH$_3$ | 1-Ethylallyl | CH=CH |
| CF$_3$ | CH$_3$ | 1-Methyl-2-butenyl | CH=CH |
| CF$_3$ | CH$_3$ | 1-Ethyl-2-butenyl | CH=CH |
| CF$_3$ | CH$_3$ | Cyclopropyl | CH=CH |
| CF$_3$ | CH$_3$ | Cyclobutyl | CH=CH |
| CF$_3$ | CH$_3$ | Cyclopentyl | CH=CH |
| CF$_3$ | CH$_3$ | Cyclohexyl | CH=CH |
| CF$_3$ | CH$_3$ | 2-Cyclopentenyl | CH=CH |
| CF$_3$ | CH$_3$ | 1-Cyclopentenyl | CH=CH |
| CF$_3$ | CH$_3$ | 2-Cyclohexenyl | CH=CH |
| CF$_3$ | CH$_3$ | 1-Cyclohexenyl | CH=CH |
| CF$_3$ | CH$_3$ | Phenyl | CH=CH |
| CH$_3$ | CH$_3$ | C$_2$H$_5$ | CH=CH |
| CH$_3$ | CH$_3$ | i-C$_3$H$_7$ | CH=CH |
| CH$_3$ | CH$_3$ | n-C$_3$H$_7$ | CH=CH |
| CH$_3$ | CH$_3$ | n-C$_4$H$_9$ | CH=CH |
| CH$_3$ | CH$_3$ | sec.-C$_4$H$_9$ | CH=CH |
| CH$_3$ | CH$_3$ | i-C$_4$H$_9$ | CH=CH |
| CH$_3$ | CH$_3$ | tert.-C$_4$H$_9$ | CH=CH |
| CH$_3$ | CH$_3$ | n-C$_5$H$_{11}$ | CH=CH |
| CH$_3$ | CH$_3$ | sec.-C$_5$H$_{11}$ | CH=CH |
| CH$_3$ | CH$_3$ | n-C$_6$H$_{13}$ | CH=CH |
| CH$_3$ | CH$_3$ | n-C$_7$H$_{15}$ | CH=CH |
| CH$_3$ | CH$_3$ | sec.-C$_7$H$_{15}$ | CH=CH |
| CH$_3$ | CH$_3$ | 1-Methylvinyl | CH=CH |
| CH$_3$ | CH$_3$ | 2-Methylvinyl | CH=CH |
| CH$_3$ | CH$_3$ | Allyl | CH=CH |
| CH$_3$ | CH$_3$ | 2-Methylallyl | CH=CH |
| CH$_3$ | CH$_3$ | 2-Ethylallyl | CH=CH |
| CH$_3$ | CH$_3$ | 1-Methylallyl | CH=CH |
| CH$_3$ | CH$_3$ | 1-Ethylallyl | CH=CH |
| CH$_3$ | CH$_3$ | 1-Methyl-2-butenyl | CH=CH |
| CH$_3$ | CH$_3$ | 1-Ethyl-2-butenyl | CH=CH |
| CH$_3$ | CH$_3$ | Cyclopropyl | CH=CH |
| CH$_3$ | CH$_3$ | Cyclobutyl | CH=CH |
| CH$_3$ | CH$_3$ | Cyclopentyl | CH=CH |
| CH$_3$ | CH$_3$ | Cyclohexyl | CH=CH |
| CH$_3$ | CH$_3$ | 2-Cyclopentenyl | CH=CH |
| CH$_3$ | CH$_3$ | 1-Cyclopentenyl | CH=CH |
| CH$_3$ | CH$_3$ | 2-Cyclohexenyl | CH=CH |
| CH$_3$ | CH$_3$ | 1-Cyclohexenyl | CH=CH |
| CH$_3$ | CH$_3$ | Phenyl | CH=CH |

The novel active ingredients are particularly suitable for protecting various materials against degradation or destruction by bacteria or fungi or from being attacked by and covered with microorganisms. Examples of materials which can be preserved or microbicidally finished with the novel active ingredients are glues and adhesives, starch solutions, wax emulsions, clay emulsions, sizes, finishes, spinning baths, gelatine formulations, putty, joint sealants, cooling lubricants, drilling oils, fuels, plastic dispersions, emulsion paints, textiles, leather, raw hides and cosmetics. The compounds are also suitable as anti-slime agents in the paper industry, in cooling towers and in air moistening units.

The compounds I are also suitable for protecting the following plant species against attack by microorganisms: cereals (e.g., wheat, barley, rye, oats, rice, sorghum and related species); beets (e.g., sugar and fodder beets); pomes, drupes and aggregate fruit (e.g., apples, pears, plums, peaches, almonds, cherries, strawberries, raspberries and blackberries); legumes (e.g., beans, lentils, peas, soybeans); oil-yielding crops (e.g., rape, mustard, poppies, olives, sunflowers, coconuts, castor-oil beans, cocoa beans, groundnuts); cucurbits (e.g., pumpkins, cucumbers, melons); fiber-yielding plants (e.g., cotton, flax, hemp, jute); citrus fruit (e.g., oranges, lemons, grapefruit, tangerines); vegetables (e.g., spinach, lettuce, asparagus, cabbage varieties, carrots, onions, tomatoes, potatoes, paprika); laurel species (e.g., avocado, cinnamomum, camphor) or plants such as Indian corn, tobacco, nuts, coffee, sugar cane, tea, grapes, hops, and banana and rubber trees. For the purposes of the present invention, the term "plants" is also taken to mean all types of other green growth, whether ornamentals, grassy areas, embankments, or generally low-growing cover crops.

For example the following microorganisms may be combatted with the novel compounds I: *Straphylococcus aureus, Escherichia coli, Klebsielle pneumoniae, Citrobacter freundii, Proteus vulgaris, Pseudomonas aeruginosa, Desulfovibrio desulfuricans, Streptoverticillium rubrireticuli, Aspergillus niger, Aspergillus versicolor, Penicillium funiculosum, Penicillium expansum, Penicillium glaucum, Paecilomyces variotii, Trichoderma viride, Chaetomium globosum, Aspergillus amstelodami, Phoma pigmentovora, Phoma violacea, Aureobasidium pullulans, Saccharomyces cerevisiae, Alternaria tenuis, Stemphylium macrosporoideum, Cladosporium herbarum, Cladosporium resinae, Candida albicans, Trichophyton mentagrophytes, Geotrichum candidans, Monilia sitophila, Scenedesmus quadricauda, Chlorella vulgaris, Nostoc muscorium, Oscillatoria limosa* and *Anabaena constricta.*

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin-sulfite waste liquors and methylcellulose.

The formulations generally contain from 0.1 to 95, and preferably from 0.5 to 90, wt. % of active ingredient. The active ingredients are used in a purity of from 90 to 100, and preferably from 95 to 100, % (according to the NMR/HPLC/GC spectrum).

Usual application concentrations are—based on the weight of the material to be protected—from 0,001 to 5, and preferably from 0.01 to 2, wt. % of active ingredient; when the active ingredients are used for treating water, in oil production, in drilling and cutting oils, fuels, in swimming baths, cooling towers, air moistening units or in the paper industry, amounts of from 5 to 500 ppm are sufficient. Ready-to-use disinfectant solutions contain for instance from 0.5 to 10 wt. % of active ingredient.

Examples of such formulations are given below:

I. A solution of 90 parts by weight of compound no. 3 and 10 parts by weight of N-methyl-α-pyrrolidone, which is suitable for application in the form of very fine drops.

II. A mixture of 20 parts by weight of compound no. 5, 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By finely dispersing the mixture in 100,000 parts by weight of water, an aqueous dispersion is obtained.

III. An aqueous dispersion of 20 parts by weight of compound no. 2, 40 parts by weight of cyclohexanone, 30 parts by weight of isobutanol, 20 parts by weight of the adduct of 40 moles of ethylene oxide and 1 mole of castor oil. A mixture of this dispersion with 100,000 parts by weight of water contains 0.02 wt. % of the active ingredient.

IV. An aqueous dispersion of 20 parts by weight of compound no. 4, 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. The mixture of this dispersion with 100,000 parts by weight of water contains 0.02 wt. % of the active ingredient.

V. A hammer-milled mixture of 80 parts by weight of compound no. 1, 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel. By finely dispersing the mixture in 20,000 parts by weight of water, a spray liquor containing 0.1 wt. % of the active ingredient is obtained.

VI. An intimate mixture of 3 parts by weight of compound no. 6 and 97 parts by weight of particulate kaolin. The dust contains 3 wt. % of the active ingredient.

VII. An intimate mixture of 30 parts by weight of compound no. 9, 92 parts by weight of powdered silica gel and 8 parts by weight of paraffin oil sprayed onto the surface of this silica gel. This formulation of the active ingredient exhibits good adherence.

VIII. A stable aqueous dispersion of 40 parts by weight of compound no. 7, 10 parts of the sodium salt of a phenolsulfonic acid-urea-formaldehyde condensate, 2 parts of silica gel and 48 parts of water, which dispersion can be further diluted.

IX. A stable oily dispersion of 20 parts by weight of compound no. 8, 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil.

X. A hammer-milled mixture of 10 parts by weight of compound no. 10, 4 parts by weight of the sodium salt of diisobutylnaphthalene-α-sulfonic acid, 20 parts by weight of the sodium salt of a lignin-sulfonic acid obtained from a sulfite waste liquor, 38 parts by weight of silica gel, and 38 parts by weight of kaolin. By finely dispersing the mixture in 10,000 parts by weight of water, a spray liquor containing 0.1 wt. % of the active ingredient is obtained.

Used alone, the active ingredients act as low-foaming biocides. A significant increase in the action of biocidal formulations containing these compounds is achieved if tri-$C_6$- to $C_{12}$-alkylmethylammonium salts, preferably in amounts of from 20 to 40 wt. %, based on the weight of compounds of the general formula I, are added.

The active ingredients may also be mixed with other, prior art, microbicides. In many instances, a synergistic effect is achieved, i.e., the microbicidal action of the mixture is greater than the added actions of its individual components.

Prior art microbicides may be added to the novel substances in a weight ratio of from 1:100 to 100:1.

Examples of such active ingredients are as follows:
2-(thiocyanomethylthio)-benzothiazole
1-[2-(2,4-dichlorophenyl)-2-(2-propenyloxy)-ethyl]-1H-imidazole
2,4,5,6-tetrachloroisophthalodinitrile
methylene bisthiocyanate
tributyltin oxide, naphthenate, benzoate, salicylate mercaptobenzothiazole
1,2-benzisothiazolone and its alkali metal salts
alkali metal compounds of N'-hydroxy-N-cyclohexyl-diazenium oxide
2-(methoxycarbonylamino)-benzimidazole
2-methyl-3-oxo-5-chlorothiazolin-3-one
trihydroxymethylnitromethane
glutardialdehyde
chloroacetamide
polyhexamethylene bisguanide
5-chloro-2-methyl-4-isothiazolin-3-one + magnesium salts
3,5-dimethyltetrahydro-1,3,5-2H-thiadiazine-2-thione
hexahydrotriazine
N,N-methylolchloroacetamide
2-n-octyl-4-isothiazolin-3-one
oxazolidines
bisoxazolidines
2,5-dihydro-2,5-dialkoxy-2,5-dialkylfurans
diethyldodecylbenzylammonium chloride
dimethyloctadecyldimethylbenzylammonium chloride
dimethyldidecylammonium chloride
dimethyldidodecylammonium chloride
trimethyltetradecylammonium chloride
benzyldimethylalkyl-($C_{12}$-$C_{18}$)-ammonium chloride
dichlorobenzyldimethyldodecylammonium chloride
cetylpyridinium chloride
cetylpyridinium bromide
cetyltrimethylammonium chloride
laurylpyridinium chloride
laurylpyridinium bisulfate
benzyldodecyldi(beta-oxyethyl)-ammonium chloride dodecylbenzyltrimethylammonium chloride
n-alkyldimethylbenzylammonium chloride
(alkyl radical: 40% $C_{12}$, 50% $C_{14}$, 10% $C_{16}$)
lauryldimethylethylammonium ethyl sulfate
n-alkyldimethyl-(1-naphthylmethyl)-ammonium chloride
(alkyl radical: 98% $C_{12}$, 2% $C_{14}$)
cetyldimethylbenzylammonium chloride
lauryldimethylbenzylammonium chloride Examples of further compounds which may be admixed are:
1,3-dimethylol-5,5-dimethylhydantoin
dimethylolurea
tetramethylolacetylenediurea
dimethylolglyoxalmonoureine
hexamethylenetetramine
glyoxal
glutardialdehyde
N-methylolchloroacetamide
1-(hydroxymethyl)-5,5-dimethylhydantoin
1,3-bis-(hydroxymethyl)-5,5-dimethylhydantoin
imidazolidinylurea
1-(3-chloroallyl)-3,5,7-triaza-1-azonia-adamantan chloride
1,3-bis-(β-ethylhexyl)-5-methyl-5-amino-hexahydropyrimidine
1,3,5-tris-(hydroxyethyl)-1,3,5-hexahydrotriazine
1,2-dibromo-2,4-dicyanobutane
5-bromo-5-nitro-1,3-dioxane
2-bromo-2-nitropropanediol
1,1'-hexamethylene-bis-[5-(4-chlorophenyl)-biguanide]
4,4-diaminodiphenoxypropane
2-bromo-2-nitropropane-1,3-diol
sorbic acid and its salts
p-hydroxybenzoic acid and its esters and salts
zinc-2-pyridinethiol-N-oxide
2-[(hydroxylmethyl)amino]-ethanol
dithio-2,2'-bis(benzmethylamide)
5-chloro-2-(2,4-dichlorophenoxy)-phenol
thio-bis-(4-chlorophenol)
o-phenylphenol
chloromethyl-diiodomethylsulfone
p-chlorophenyl-3-iodopropargylformal.

Synthesis Examples

The directions given in the synthesis examples below were used, after appropriate modification of the starting materials, to obtain further compounds I. The compounds thus obtained are listed in the tables below with their physical data.

1. N-[2-(1-Methylpropyl)-cyclohexyl]-2-methyl-4-trifluoromethyl-thiazole-5-carboxamide At 0° C., 3.4 g of 2-methyl-4-trifluoromethylthiazole-5-carboxylic chloride is dripped into a solution of 2.3 g of trans-2-sec.-butylcyclohexylamine and 1.5 g of triethylamine in 15 ml of tetrahydrofuran, and the mixture is stirred for 2 hours at 25° C. The batch is diluted with 300 ml of water, extracted twice with tert-butyl methyl ether and dried, the solvent is evaporated off, and the residue is made into a paste with a small amount of pentane. There is isolated 2.3 g of 2-methyl-4-trifluoromethyl-thiazole-5-carboxylic acid-trans-2-sec-butylcyclohexylamide of m.p. 112°–113° C.

TABLE 1

IA

| No. | R | A | m.p. (°C.) |
|---|---|---|---|
| 1.01 | $CH(CH_3)CH_2CH_3$ | 2-$CF_3$—$C_6H_4$ | 117–119 |
| 1.02 | $CH(CH_3)CH_2CH_3$ | 2-$CH_3$—$C_6H_4$ | 113–116 |
| 1.03 | $CH(CH_3)CH_2CH_3$ | 2-Br—$C_6H_4$ | 122–124 |
| 1.04 | $CH_2CH_3$ | 2-Cl-pyridin-3-yl | 190–191 |
| 1.05 | $CH(CH_3)_2$ | 2-Cl-pyridin-3-yl | 134–136 |
| 1.06 | $CH(CH_3)CH_2CH_3$ | 2-Cl-pyridin-3-yl | oil |
| 1.07 | $CH(CH_3)CH_2CH_3$ | 2-$CH_3$-5,6-dihydro-[4H]-pyran-3-yl | 128–130 |
| 1.08 | $CH(CH_3)CH_2CH_3$ | 3-$CH_3$-5,6-dihydro-1,4-oxathiin-2-yl | 94–98 |
| 1.09 | $CH(CH_3)CH_2CH_3$ | 3-$CH_3$-furan-3-yl | 102–104 |
| 1.10 | $CH(CH_3)CH_2CH_3$ | 3-$CH_3$, 4-$CF_3$-thiazol-5-yl | 112–113 |
| 1.11 | $CH(CH_3)CH_2CH_3$ | 2,4-$(CH_3)_2$-thiazol-5-yl | 89–92 |
| 1.12 | $CH_2CH_2CH_3$ | 2-Cl-pyridin-3-yl | 145–147 |
| 1.13 | $CH_2CH_2CH_3$ | 2,4-$(CH_3)_2$-thiazol-5-yl | 126–127 |
| 1.14 | $CH_2CH_2CH_3$ | 3-$CH_3$, 4-$CF_3$-thiazol-5-yl | 147–148 |
| 1.15 | $CH_2CH_2CH_2CH_3$ | 2-Cl-pyridin-3-yl | 126–129 |
| 1.16 | $CH_2CH_2CH_2CH_3$ | 2,4-$(CH_3)_2$-thiazol-5-yl | 115–117 |
| 1.17 | $CH_2CH_2CH_2CH_3$ | 3-$CH_3$, 4-$CF_3$-thiazol-5-yl | 123–125 |
| 1.18 | Cyclohexyl | 2-Cl-pyridin-3-yl | 126–128 |
| 1.19 | Cyclohexyl | 2, 4-$(CH_3)_2$-thiazol-5-yl | 138–142 |
| 1.20 | Cyclohexyl | 3-$CH_3$, 4-$CF_3$-thiazol-5-yl | 167–171 |
| 1.21 | $CH_2CH(CH_3)_2$ | 2-Cl-pyridin-3-yl | 148–150 |
| 1.22 | Cyclohexen-1-yl | 2-Cl-pyridin-3-yl | 130–131 |
| 1.23 | Cyclohexen-1-yl | 2-$CF_3$—$C_6H_4$ | 130–133 |
| 1.24 | Cyclohexen-1-yl | 2-$CH_3$-furan-3-yl | 114–119 |
| 1.25 | Cyclohexen-1-yl | 3-$CH_3$, 4-$CF_3$-thiazol-5-yl | 120–121 |
| 1.26 | Cyclohexen-1-yl | 2,4-$(CH_3)_2$-thiazol-5-yl | 110–112 |
| 1.27 | Cyclohexen-1-yl | 1,3-$(CH_3)_2$-pyrazol-4-yl | 174–177 |
| 1.28 | $CH_2C_6H_5$ | 2-Cl-pyridin-3-yl | 161–162 |
| 1.29 | $CH_2C_6H_5$ | 2,4-$(CH_3)_2$-thiazol-5-yl | 177–178 |
| 1.30 | $CH_2C_6H_5$ | 3-$CH_3$, 4-$CF_3$-thiazol-5-yl | 178–179 |
| 1.31 | $C_6H_5$ | 2-Cl-pyridin-3-yl | 143–144 |
| 1.32 | $C_6H_5$ | 2,4-$(CH_3)_2$-thiazol-5-yl | 142–144 |
| 1.33 | $C_6H_5$ | 3-$CH_3$, 4-$CF_3$-thiazol-5-yl | 136–137 |
| 1.34 | 4-F—$C_6H_4$ | 2-Cl-pyridin-3-yl | 145–150 |
| 1.35 | 4-F—$C_6H_4$ | 2,4-$(CH_3)_2$-thiazol-5-yl | 174–175 |
| 1.36 | 4-F—$C_6H_4$ | 3-$CH_3$, 4-$CF_3$-thiazol-5-yl | 152–153 |
| 1.37 | 4-$OCH_3$—$C_6H_4$ | 2-Cl-pyridin-3-yl | 111–113 |
| 1.38 | 4-$OCH_3$—$C_6H_4$ | 3-$CH_3$, 4-$CF_3$-thiazol-5-yl | 132–134 |

TABLE 2

IB

| No. | R | A | m.p. (°C.) |
|---|---|---|---|
| 2.01 | $C_6H_5$ | 2-Cl-pyridin-3-yl | 157–160 |
| 2.02 | $C_6H_5$ | 2,4-$(CH_3)_2$-thiazol-5-yl | 131–133 |
| 2.03 | $C_6H_5$ | 3-$CH_3$, 4-$CF_3$-thiazol-5-yl | 112–114 |

Examples illustrating the biological action:
Action on Botrytis cinerea

Slices of green paprika pods were sprayed to runoff with aqueous formulations containing (dry basis) 80% of active ingredient and 20% of emulsifier. After the sprayed-on layer had dried, the slices were inoculated with a spore suspension of Botrytis cinerea which contained $1.7 \times 10^6$ spores per ml of a 2% strength biomalt in water solution. The inoculated slices were then kept for 4 days in a high-humidity atmosphere.

After this period, the controls exhibited 90% fungus attack, whereas the paprika slices treated with 500 ppm of compounds nos. 5, 6, 7, 8, 9, 10, 11, 12, 13, 15, 16, 19, 24, 25, 26, 27 and 32 exhibited 15% attack at most.

At an application rate of 1000 ppm of compounds nos. 4, 5 and 6, the treated paprika slices exhibited at most 15% attack, whereas 40 the slices treated with 1000 ppm of N-(2-methylcyclohexyl)-2-chloronicotinamide exhibited 40% attack.

We claim:

1. An N-cyclohex(en)ylcarboxamide of the formula I

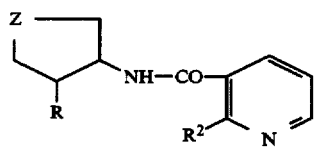

$R^1$ is $C_2-C_{12}$-alkyl, $C_2-C_{12}$-alkoxy, $C_3-C_{12}$-alkenyl, $C_3-C_{12}$-alkenyloxy, $C_3-C_6$-alkynyl or $C_3-C_6$-alkynyloxy, where these groups can be partially or completely halogenated; $C_3-C_7$-cycloalkyl, $C_4-C_7$-cycloalkenyl, $C_3-C_7$-cycloalkyloxy or $C_4-C_7$-cycloalkenyloxy, where these rings can carry from one to three $C_1-C_4$-alkyl groups; phenyl or benzyl, where the phenyl rings can each carry from one to five halogen atoms and/or from one to three of the following radicals: $C_1-C_4$-alkyl, $C_1-C_4$-haloalkyl, $C_1-C_4$-alkoxy, $C_1-C_4$-haloalkoxy, $C_1-C_4$-alkylthio or $C_1-C_4$-haloalkylthio;

Z is $CH_2CH_2$ or $CH=CH$ and
$R^2$ is halogen, $C_1-C_4$-alkyl or $C_1-C_4$-haloalkyl;
where the R and

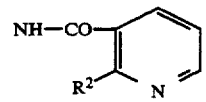

are trans to each other; and with the proviso that R cannot be $C_2-C_3$-alkyl and Z cannot be ethyl at the same time.

2. An n-cyclohex(en)ylcarboxamide of the formula I as claimed in claim 1, where R has the meanings given in claim 1 and $R^2$ is halogen or $C_1$-haloalkyl.

3. An N-cyclohex(en)ylcarboxamide of the formula I as claimed in claim 1, where R has the meanings given in claim 1 and $R^2$ is chloro or trifluoromethyl.

4. An agent for combatting harmful fungi and containing a fungicidally effective of a compound of the formula I as claimed in claims 1, 2 or 3 and inert additives.

5. A method of combatting harmful fungi, wherein the fungi, their habitat and/or the plants or materials to be kept free from fungi are treated with a fungicidally effective amount of a compound of the formula I as claimed in claims 1, 2 or 3.

6. A member selected from the group consisting of 2-chloronicotinic acid-trans-2'-ethylcyclohexylamide, 2-chloronicotinic acid-trans2'-n-propylcyclohexylamide and 2-chloronicotinic acid-trans-2'-isopropylcyclohexylamide.

* * * * *

UNITED STATES PATENT AND TRADEMARK OFFICE
CERTIFICATE OF CORRECTION

PATENT NO.: 5,416,103

DATED: May 16, 1995

INVENTOR(S): EICKEN et al.

It is certified that error appears in the above-identified patent and that said Letters Patent is hereby corrected as shown below:

On the title page, item [54], the title should read as follows:
--N-CYCLOHEX(EN)YLCARBOXAMIDES AND COMPOSITIONS CONTAINING THEM FOR CONTROLLING FUNGAL PESTS--.

Column 30, claim 2, line 1, " n- " should read -- N- --.

Column 30, claim 4, line 3, replace "claims" with --claim--; delete "2 or 3".

Column 30, claim 5, line 5, replace "claims 1, 2 or 3" with --claim 1--.

Signed and Sealed this

Fifth Day of September, 1995

Attest:

BRUCE LEHMAN

*Attesting Officer*  *Commissioner of Patents and Trademarks*